(12) United States Patent
Haynes et al.

(10) Patent No.: US 10,556,398 B2
(45) Date of Patent: Feb. 11, 2020

(54) ARRAYS AND METHODS OF MANUFACTURE

(71) Applicant: Digital Sensing Limited, Auckland (NZ)

(72) Inventors: Andrew Haynes, Auckland (NZ); David James Bates, Auckland (NZ); Ashton Cyril Partridge, Auckland (NZ); Karthik Kannappan, Auckland (NZ)

(73) Assignee: Digital Sensing Limited, Auckland (NZ)

( * ) Notice: Subject to any disclaimer, the term of this patent is extended or adjusted under 35 U.S.C. 154(b) by 0 days.

(21) Appl. No.: 14/351,832

(22) PCT Filed: Oct. 12, 2012

(86) PCT No.: PCT/NZ2012/000183
§ 371 (c)(1),
(2) Date: Apr. 14, 2014

(87) PCT Pub. No.: WO2013/055234
PCT Pub. Date: Apr. 18, 2013

(65) Prior Publication Data
US 2014/0342128 A1 Nov. 20, 2014

(30) Foreign Application Priority Data

Oct. 14, 2011 (NZ) ........................................ 595774

(51) Int. Cl.
*B32B 3/30* (2006.01)
*B05D 5/00* (2006.01)
(Continued)

(52) U.S. Cl.
CPC .................. *B32B 3/30* (2013.01); *B05D 5/00* (2013.01); *C25D 1/003* (2013.01);
(Continued)

(58) Field of Classification Search
CPC .. B32B 3/085; B32B 3/12; B32B 3/14; B32B 3/26; B32B 3/263; B32B 3/30;
(Continued)

(56) References Cited

U.S. PATENT DOCUMENTS 5,118,403 A   6/1992  Magee et al.
6,093,302 A * 7/2000  Montgomery ....... B01J 19/0046
                                                    205/122
(Continued)

FOREIGN PATENT DOCUMENTS

EP          2204650          7/2010
JP          H09-504910       5/1997
(Continued)

*Primary Examiner* — Megha M Gaitonde
(74) *Attorney, Agent, or Firm* — Foley & Lardner LLP

(57) ABSTRACT

The invention relates to a microarray structure including a substrate material layer, a continuous three-dimensional (3D) surface layer on the substrate material layer that is capable of functionalisation for use as an array, and an inert material wherein the structure includes accurately defined and functionalisable isolated areas which are millimeter to nanometer in size. The functionalised areas are part of the continuous 3D surface layer and are isolated by the inert material and are interconnected within the structure by the continuous 3D surface layer.

22 Claims, 26 Drawing Sheets

(51) Int. Cl.
*C25D 1/00* (2006.01)
*G01N 27/327* (2006.01)

(52) U.S. Cl.
CPC .... *G01N 27/3275* (2013.01); *B32B 2307/202* (2013.01); *Y10T 428/24612* (2015.01)

(58) Field of Classification Search
CPC ....... B32B 15/04; B32B 2255/06; B05D 5/00; B05D 5/12; G01N 27/3275; Y10T 428/24174; Y10T 428/24479; Y10T 428/24521; Y10T 428/24545; Y10T 428/24612; Y10T 428/2462; Y10T 428/24802; B81B 7/04; B81B 2201/02
USPC .... 428/119, 156, 161, 164, 172, 173, 195.1, 428/212, 213
See application file for complete search history.

(56) References Cited

U.S. PATENT DOCUMENTS

| | | | |
|---|---|---|---|
| 2002/0187249 A1 | 12/2002 | Pluster | |
| 2003/0230967 A1* | 12/2003 | Kawamura | B41M 3/006 313/483 |
| 2004/0110277 A1 | 6/2004 | Maeda | |
| 2004/0126766 A1* | 7/2004 | Amorese | B01L 3/50853 435/6.12 |
| 2005/0008821 A1 | 1/2005 | Pricone | |
| 2005/0029095 A1 | 2/2005 | Hall et al. | |
| 2006/0043638 A1 | 3/2006 | Corrigan et al. | |
| 2006/0057023 A1 | 3/2006 | Thompson et al. | |
| 2008/0119372 A1 | 5/2008 | Hah et al. | |
| 2008/0169059 A1 | 7/2008 | Messersmith et al. | |
| 2009/0028910 A1 | 1/2009 | Desimone et al. | |
| 2009/0042741 A1 | 2/2009 | Northern | |
| 2011/0111182 A1* | 5/2011 | Stay | H05K 3/107 428/173 |

FOREIGN PATENT DOCUMENTS

| | | |
|---|---|---|
| JP | H09-292360 | 11/1997 |
| JP | H10-325821 | 12/1998 |
| JP | 2001-522999 A | 11/2001 |
| JP | 2004-045394 | 2/2004 |
| JP | 2004-333404 A | 11/2004 |
| JP | 2007-501389 A | 1/2007 |
| JP | 2009128041 | 6/2009 |
| WO | WO-2002/059372 | 10/2001 |
| WO | WO-2002/043937 | 10/2002 |
| WO | WO-03/087798 | 10/2003 |
| WO | WO-2006/023324 | 8/2005 |
| WO | WO 2010002679 A2 * | 1/2010 ............ H05K 3/107 |
| WO | WO-2011/012971 | 10/2011 |
| WO | WO-2011/129710 | 10/2011 |

* cited by examiner

A

B $R_{ct}$ - Charge tranfer resistance
$C_{dl}$ - Double layer capacitance
$R_s$ - Solution resistance
$C_s$ - Solution capacitance

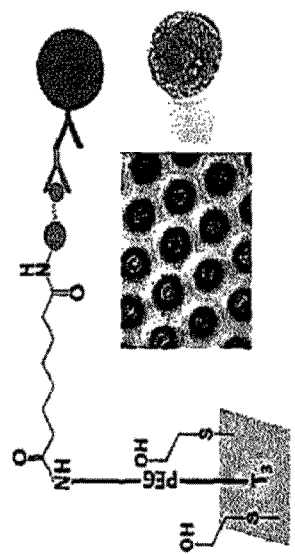
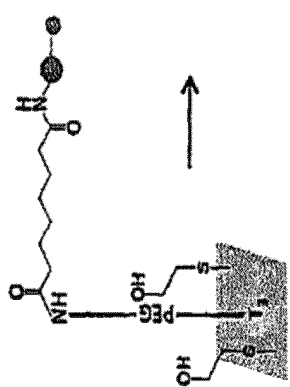
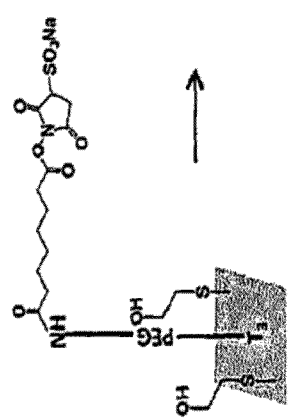
Figure 37A
Figure 37B
Figure 37C

ARRAYS AND METHODS OF MANUFACTURE

CROSS REFERENCE TO RELATED APPLICATIONS

This application is the National Stage of International Application No. PCT/NZ2012/000183, filed on Oct. 12, 2012, which claims the benefit of New Zealand Application No. 595774, filed on Oct. 14, 2011 The contents of both applications are hereby incorporated by reference in their entirety.

TECHNICAL FIELD

The invention relates to the development of a 3D ("three dimensional") surface which can be modified to form an array of isolated but interconnected functionalisable areas for use in a variety of array applications, in particular microelectrode sensor arrays and microcatalyst arrays. In particular, the method allows for the fabrication of arrays which include isolated but conductively interconnected surface areas which can be arranged in a variety of patterns. The invention also relates to such arrays.

BACKGROUND ART

There are currently a number of known methods for fabricating arrays. These include printing techniques such as screen printing or ink jet printing, lithographic techniques whereby the array is etched onto a surface, photolithography, direct electrodeposition (deposition of wires), patterning of carbon nanotube/nanofiber arrays and assembly techniques, for example, wires set in an epoxy resin. However, these known methods have a number of limitations. In particular, they are cumbersome to carry out and it is difficult to accurately define the arrays over a large surface area and on the millimeter to nanometer scale. Thus, the resolution of the arrays produced is often poor due largely to that lack of definition. The inability to accurately place sensor sites on such arrays causes problems as qualitative and quantitative measurement is detrimentally affected. In particular, issues of cost arise with the fabrication of nanoscale arrays as, while they can be made, control over definition and cost remain problems which cannot be easily overcome. Economy of scale is a particular issue.

The fabrication of arrays on the millimeter to nanometer scale, particularly on the micrometer to nanometer scale over large surface areas having improved accuracy of definition would be particularly valuable in the areas of sensing, electrochemistry and catalysis. Electrochemistry is the branch of chemistry that deals with the use of spontaneous chemical reactions to produce electricity, and the use of electricity to bring about non-spontaneous chemical change. In particular, it is the study of aqueous chemical reactions which occur at the interface of an electron conductor such as a metal or a semiconductor (the electrode) and an ionically conducting medium (the electrolyte) and which involve electron transfer between the electrode and the electrolyte or species in solution. Catalysis concerns the creation of a new reaction pathway with a lower activation energy, thereby allowing more reactant molecules to cross the reaction barrier and form reaction products.

In a typical electrochemical detection process it is, in general, preferable to employ an array of smaller electrodes as opposed to a single large electrode. Reasons for this include:

the ability to use smaller sample volumes;
application in both in vivo and in vitro measurement;
low depletion rate of target molecules;
low background charging due to their reduced surface area;
reduced IR drop; and
high current density arising from enhanced mass transport to the electrode surface as a result of convergent diffusion.

Accurately defined arrays would also be valuable for use in:

the analysis of fluids (e.g. biological: blood, urine, milk and non-biological: waste water streams, beverages);
integration with living, biological systems into lab-on-a-chip devices,
in vitro or in vivo biological sensing such as enzyme-linked assays and the detection of many other biomolecules;
catalysis;
trace metal monitoring in the environment;
corrosion monitoring; and
energy production and storage devices.

Co-pending PCT application number PCT/2011/000052 also concerns microarray structures. However, the microarrays as described in PCT/2011/00052 simply include a continuous inert base substrate with functionalisable areas isolated by an inert material. The functionalisable areas are not stated to be conductively interconnected and the structures do not include at least one continuous interconnected layer, separate to the base substrate material and inert material, that allows for improved functional and structural flexibility of the microarrays formed.

It is therefore an object of the present invention to provide arrays including isolated but conductively interconnected functionalisable areas and/or methods of forming such arrays. It is a further or alternative object of the present invention to at least provide the public with a useful choice.

SUMMARY OF THE INVENTION

In a first aspect, the present invention provides a microarray structure including a substrate material layer, a continuous 3D ("three-dimensional") surface layer on the substrate material layer that is capable of functionalisation for use as an array, and an inert material;

wherein the structure includes accurately defined and functionalisable isolated areas which are millimeter to nanometer in size; and wherein the functionalisable areas are part of the continuous 3D surface layer and are isolated by the inert material but which are interconnected within the structure by the continuous 3D surface layer.

Preferably, the continuous 3D surface layer is electrically conductive. More preferably, the 3D surface layer is a metal.

Alternatively, the continuous 3D surface layer is a carbon based material, including but not limited to carbon fiber, carbon paste, graphite, graphene, glassy carbon, carbon nanotubes and conducting polymers.

Preferably, the continuous 3D surface layer is a unitary layer that covers the substrate material layer.

Preferably, the continuous 3D surface layer is cut into a plurality of isolated continuous 3D surface layer segments on the substrate material layer, each segment including a plurality of functionalisable areas, wherein each group of functionalisable areas is capable of separate functionalisation.

Optionally, the inert material is also an insulating material.

Optionally, the substrate material layer is formed from a conductive material or a non-conductive inert material which, optionally, is also an insulating material.

Optionally, the structure includes an adhesion layer between the continuous 3D surface layer and the substrate material layer.

Preferably, the microarray structure is functionalised to be a micro-electrode sensor array and/or a micro-catalyst array.

Preferably, the continuous 3D surface layer protrudes from the inert material such that the functionalisable areas are exposed above the inert material.

Preferably, the inert material and the functionalisable areas form a 2D ("two-dimensional") surface including functionalisable areas.

In a second aspect, the present invention provides an intermediate structure for use in fabricating an array according to the first aspect of the invention, the intermediate structure including a substrate material layer that includes an accurately defined 3D pattern to a millimeter to nanometer scale, and a continuous 3D surface layer on the substrate material layer that is capable of functionalisation for use as an array over at least part of the pattern.

Preferably, substantially all the patterned area is coated with the continuous 3D surface layer.

Preferably, the substrate material layer is formed from a conductive material or a non-conductive inert material which, optionally, is also an insulating material.

Preferably, the pattern is formed by embossing, casting, stamping, etching, grinding, lithography, pressure forming, vacuum forming, roll forming, injection moulding and laser scribing/ablation.

Preferably, the substrate material layer is coated with the continuous 3D surface layer by sputtering, evaporation or electroless deposition techniques.

Preferably, the continuous 3D surface layer forms a coating layer which is electrically conductive. More preferably, the 3D coating layer is a metal.

Alternatively, the continuous 3D surface layer is a carbon based material, including but not limited to carbon fiber, carbon paste, graphite, graphene, glassy carbon, carbon nanotubes and conducting polymers.

Optionally, the intermediate structure includes an adhesion layer between the continuous 3D surface and the substrate material.

In one embodiment of the first aspect, the present invention provides an accurately defined and functionalisable array including a continuous 3D surface layer, said array formed from an intermediate structure of the second aspect of the invention, wherein a layer of inert material fills the spaces between the tips in the 3D pattern on the surface layer to give an inert material surface through, or from, which the tips of the 3D pattern protrude or are otherwise exposed; and wherein the tips are isolated by the inert material but are conductively interconnected via the continuous 3D surface layer between the inert material surface and the substrate material layer.

Optionally, the inert material surface is also an insulating layer.

In a third aspect, the present invention provides a method for the formation of an intermediate structure according to the second aspect of the invention including a continuous 3D surface layer from which an array having accurately defined and functionalisable isolated areas can be formed, the method involving the steps of:

a. placing an accurately defined 3D pattern at the millimeter to nanometer scale on the surface of a substrate material; and b. coating at least part of the patterned substrate material with a continuous 3D surface layer.

Preferably, the pattern is placed on the surface of the substrate material by embossing, casting, stamping, etching, grinding, lithography, pressure forming, vacuum forming, roll forming, injection moulding and laser scribing/ablation.

Preferably, the substrate material is coated with the continuous 3D surface layer by sputtering, evaporation or electroless deposition techniques.

Preferably, the continuous 3D surface layer covers substantially all of the patterned area of the substrate material.

Alternatively, the continuous 3D surface layer is cut into a plurality of isolated continuous 3D surface layer segments, wherein the plurality of segments cover substantially all of the patterned area of the substrate material.

Optionally, the method includes the step of adding an adhesion layer between the substrate material and the continuous 3D surface layer.

Preferably, an inert material is placed on the continuous 3D surface to form a structure according to the first aspect of the invention.

In a fourth aspect, the present invention provides a method for the formation of a structure capable of functionalisation as an array according to the first aspect of the invention, the method including the steps of taking the intermediate structure according to the second aspect of the invention and filling individual spaces between the tips of the 3D pattern on the intermediate structure with an inert material to give a surface through, or from, which the tips of the 3D pattern protrude or are otherwise exposed; wherein the tips form functionalisable areas which are isolated by the inert material but are interconnected within the structure by the continuous 3D surface layer and are capable of functionalisation.

Optionally, the tops of the tips can be cut away to align with the surface of the inert material to form a 2D surface including functionalisable areas. Optionally, a portion of the inert material is also removed.

In a fifth aspect, the present invention provides a method for the formation of a 2D structure capable of functionalisation as an array, said structure including a continuous 3D surface, the method including the steps of taking the intermediate structure according to the second aspect of the invention and covering the 3D pattern on the intermediate structure with an inert material, removing sufficient of the inert filler material to only expose the tips of the 3D pattern, wherein the exposed 3D tips are isolated by the inert material but are interconnected within the structure by the continuous 3D surface and are capable of functionalisation.

In a sixth aspect, the present invention provides a further method for the formation of a structure capable of functionalisation as an array including a continuous 3D surface layer, the structure having an accurately defined 3D pattern of functionalisable areas in the millimeter to nanometer scale, the method including the steps of:

a. electroplating the continuous 3D surface layer of the intermediate structure according to the second aspect of the present invention to form a metal layer that covers the tips of the 3D pattern on the intermediate structure;

b. separating the metal layer and the substrate material of the intermediate structure to form a metal negative structure which includes a negative of the 3D pattern (the "negative 3D pattern") on the intermediate structure;

c. backfilling spaces between tips within the negative 3D pattern on the metal negative structure with an inert material to give an inert surface through, or from, which the tips of the negative 3D pattern protrude or are otherwise exposed;

d. wherein the functionalisable areas are isolated by the inert material but are interconnected within the structure.

Preferably, the metal layer covers at least substantially all of the 3D pattern on the intermediate structure.

Optionally, the tops of the tips can be cut away to align with the surface of the inert material to form a 2D surface including functionalisable areas.

In a seventh aspect, the present invention provides an intermediate structure including a continuous 3D surface capable of functionalisation for use as an array, wherein the intermediate structure includes an accurately defined 3D pattern at the millimeter to nanometer scale on at least one surface and also includes an inert material between the tips of the 3D pattern which creates a surface through, or from, which the tips of the 3D pattern protrude or are otherwise exposed, the tips of the 3D pattern thus being isolated by the inert material and being interconnected within the intermediate structure by the continuous 3D surface.

DESCRIPTION OF FIGURES

FIG. 35: shows inter-digitated tracks of an alternating working electrode and a counter electrode with a laser scribe between.

FIG. 37: (A) depicts immersion of $NH_2$ substituted arrays into a linker solution to give an activated array, according to the example method of FIG. 36; (B) depicts addition of P4-PEG-OVA to give the Haptan functionalised array, according to the example method of FIG. 36; (C) depicts exposing the array to the P4 primary antibody, and then a secondary antibody with attached beads, according to the example method of FIG. 36.

DETAILED DESCRIPTION

Figure 1:
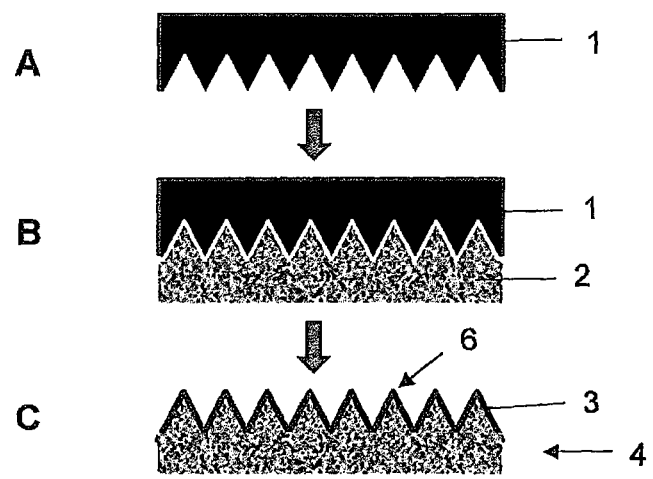
FIG. 1: shows, in schematic form, the process for preparing a coated and patterned structure 4 of the present invention.

The present invention concerns the development of arrays of various sizes for use in a variety of applications including sensors, electrochemistry and catalysis. In particular, the present invention relates to method for fabricating arrays comprising functionalisable areas at the millimeter to nanometer (inclusive) scale. These functionalisable areas are preferably conductive (but may not be) and are isolated at the surface of the array but joined below the material used to isolate them. They may be of any shape or size and can be functionalised to create sensor or catalytic sites (amongst other options) for a multitude of applications. Examples of applications include the detection of enzymatic catalysed reduction or oxidation reactions (e.g. glucose oxidase), the direct detection of oxidisable species within a solution (e.g. metals, metal oxides, organic species), the detection of antibodies, DNA, cells or small molecules where an appropriate haptan has been attached to the array surface, and detecting and binding of their complimentary antigen via an associated electrochemical method including the measurement of changes in the resistance between the binding surface and a counter electrode or an electrochemical reaction. In each instance, concentration of the target analyte is related to the level of current passed through the conductive, continuous 3D, array surface.

The microarrays of the present invention may be said to broadly consist of a substrate material on which functionalisable areas are formed. Thus, in a first aspect, the present invention provides a microarray structure, including a substrate material layer, a continuous 3D surface layer on the substrate layer that is capable of functionalisation for use as an array and an inert material. The structure includes functionalisable areas which are part of the continuous 3D surface layer and are isolated by the inert material but are interconnected within the structure by the continuous 3D surface layer.

As used herein, the "substrate material layer" (herein referred to as substrate material) refers to the base of the microarrays of the present invention. It may be flexible or rigid and is preferably planar ranging in thickness from the micrometer to millimeter scale. As will be known to a skilled person in the art, the thickness of the substrate material is primarily governed by the thickness required to ensure proper handling. Where required, the substrate material should also be optically transparent. Therefore, preferably, the substrate material is between about 50 micron to about 2 mm thick, or between about 500 micron to about 2 mm thick, or between about 50 micron to about 100 micron thick. Preferably, the substrate material is a polymer material. Alternatively, the substrate material may be a conducting material or an inert, non-conducting material. Where the substrate material layer is inert, it may also act as an insulating material. Examples of suitable flexible materials for use in the present invention include thermoplastic polyurethane, rubber, silicone rubber, and flexible epoxy. Examples of suitable rigid substrate materials for use in the present invention include glass, PMMA, PC, PS, ceramic, resin, composite materials and rigid epoxy. The substrate material may also be formed from a metal such as gold, silver, nickel or the like, as discussed in more detail below.

As used herein, "functionalisable areas" should be taken broadly to encompass those parts of the microarrays of the present invention which protrude, or are otherwise exposed, through an inert material or are exposed and are therefore capable of being functionalised as desired by a user. When the inert material protrudes through the inert material, it may be exposed above that material. The functionalisable areas can be in any shape as desired by the user and preferably form the uppermost surface or tip of a three-dimensional (3D) pillar like structure (nanometer to millimeter size) formed as part of the substrate material of the microarrays of the present invention. However, a person skilled in the art would understand that the functionalisable areas can also form the uppermost surface of a 3D rib like structure formed as part of the substrate material of the microarrays of the present invention.

Throughout the specification reference to 3D should be taken to mean a three-dimensional structure, or where required by context, a three dimensional coated structure, wherein, the three-dimensional structure is in the form of a pillar like structure or a rib like structure.

The functionalisable areas preferably range in size from the millimeter to the nanometer scale. More preferably, the functionalisable areas are between about 10 nm to about 1 micron in size, more preferably between about 200 nm to about 1 micron in size. Likewise, the spaces between individual functionalisable areas can be on the millimeter to nanometer scale.

In one embodiment of the present invention, the functionalisable areas are accurately defined areas in that they form a defined pattern on the surface of a microarray to the scale desired. This, in turn, allows a user or a computer program to pinpoint specific functionalisable areas on the surface of a microarray and make a desired measurement and allows for the functionalisation of only selected functionalisable areas on the surface of a microarray. Alternatively, the functionalisable areas are randomly arranged on the surface of a microarray of the present invention.

FIG. 1 shows, diagrammatically, the use of embossing techniques to shape the surface of the substrate material 2 into a desired 3D pattern that is accurately defined to the scale desired. FIG. 1 shows the use of a stamp to achieve this. First a stamp 1 is formed to the negative of the desired pattern (FIG. 1A). This pattern is shown in FIG. 1 as being of repeating triangles, however, this could be replaced by other options as desired by the user. The pattern does not have to be uniform. The embossing creates tips 6 that extend from the surface of the substrate material 2 and, therefore, also creates the desired spaces between those tips 6. The stamp 1 is typically made from silicon or nickel. However, it can be formed from any suitable material that is capable of use in this manner. The stamp 1 is then used to emboss the substrate material 2 with the desired pattern (FIG. 1B). As will be apparent, embossing techniques are well known and a number of other options may be available for use to create an appropriate and accurately defined pattern in a desired substrate material. These could include casting, stamping (FIG. 7C), etching, grinding, lithography, pressure forming, vacuum forming, roll forming (FIGS. 7A and 7B), injection moulding and laser scribing/ablation. Other suitable methods for forming an accurately defined pattern to the millimeter/nanometer scale would be known to those skilled in the art.

The 3D patterned substrate material 2 is then pulled away from the stamp 1 and is coated with a coating layer 3 to form a 3D coated and patterned structure 4 (FIG. 1C). The coating step forms a continuous single 3D surface over the substrate material 2.

Figure 3:
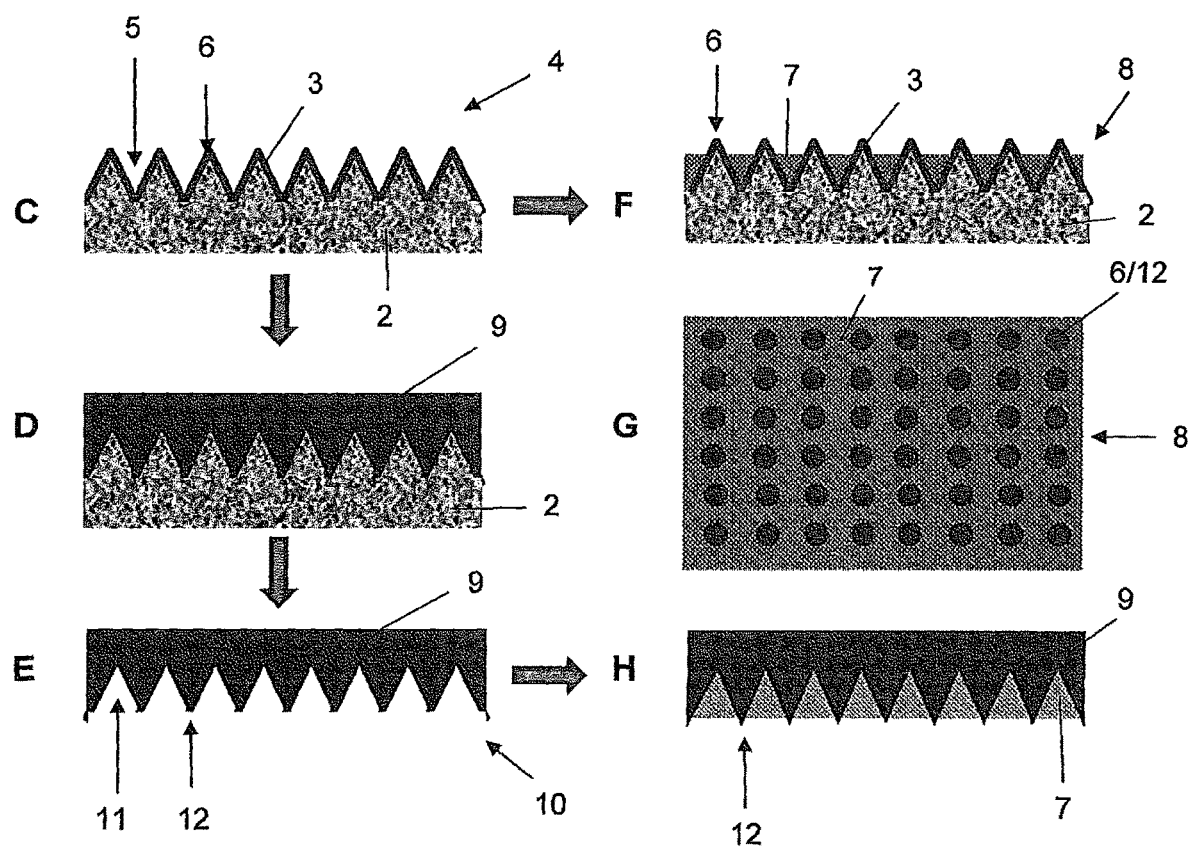
FIG. 3: shows, in schematic form, the process for converting a coated and patterned structure into an array of the present invention.

As used herein, "continuous 3D surface layer" (herein referred to as continuous 3D surface) refers to the coating layer 3 which can be formed from an electrically conductive material or a carbon-based material and which can be fabricated in large, continuous sheets over the polymer substrate material 2. Thus, the continuous 3D surface (coating layer 3) is separate from the substrate material 2 and will effectively be between the substrate material 2 and the inert material 7 (best seen in FIG. 3). The coating layer 3 (continuous 3D surface) is preferably between about 1 nm to about 5 micron thick, more preferably between about 3 nm to about 100 nm thick, more preferably about 5 nm to about 100 nm, more preferably between about 5 nm to about 50 nm thick. Preferably, the coating layer 3 (continuous 3D surface) is a unitary layer that covers the substrate material 2. Alternatively, the coating layer 3 (continuous 3D surface) is laser scribed or otherwise cut using techniques such as lithography to give a plurality of isolated continuous 3D surface layer segments on the substrate material 2. Each isolated continuous 3D surface layer segment includes a plurality of functionalisable areas so that the surface of the microarray includes a plurality of groups of functionalisable areas (FIG. 6F). Preferably, each group of functionalisable areas is capable of separate functionalisation. Preferably the coating layer 3 (continuous 3D surface) is formed from an electrically conductive material, preferably it is formed from a metal. Suitable metals for use as a coating layer 3 in the present invention include gold, platinum, silver, nickel and copper amongst others. Alternatively, the coating layer 3 is formed from a carbon-based material, preferably from the likes of carbon fiber, carbon paste, graphite, graphene, glassy carbon, carbon nanotubes and conducting polymers such as polypyrrole and polythiophene.

Application of the continuous 3D surface (coating layer 3) can be achieved by a number of methods, including but not limited to sputtering, evaporation or electroless deposition. The continuous 3D surface may be used as a seed layer as will be described later herein.

The continuous 3D surface (coating layer 3) typically includes an adhesion layer (not shown in FIG. 1) to promote adhesion to the substrate material 2. This adhesion layer therefore sits between the continuous 3D surface layer and the substrate material. Suitable adhesion materials for use in forming an adhesion layer would be known to those skilled in the art. Options would include plasma treatment of the surface to increase surface roughness, deposition of a thin layer (nanometers) of chromium or vanadium, and plasma deposited or covalently bound thiols or amines to enhance adhesion.

The inventors have found that inclusion of the continuous 3D surface in the structure of the microarrays of the present invention allows for improved functional and structural flexibility over other microarrays known in the art. In particular, the continuous 3D surface may achieve any one of a number of important roles in the present invention. For example, it protects the underlying substrate material 2 (FIG. 1). It also promotes attachment of binding chemistry at the functionalisable areas of the microarrays of the present invention. When it is formed from a conducting material, it allows electrochemical reactions to occur at the surface of the microarray at the functionalisable areas. When also formed from a conducting material, it ensures that the functionalisable areas are conductively interconnected with each other. As used herein, "conductively interconnected" refers to electrical communication of the isolated functionalisable areas of an array with each other and with an electroanalytical device such as a voltage meter, a potentiostat, a galvanostat, an impedance analyser and any other device capable of measuring current as would be known to those skilled in the art. Where the continuous 3D surface (coating layer 3) is a unitary layer covering the substrate material, it may be connected to an electroanalytical device at only one point. Alternatively, where the continuous 3D surface (coating layer 3) has been laser scribed or otherwise cut into isolated continuous 3D surface layer segments, each segment may not necessarily be interconnected with other segments in the wider array structure and each may be connected to an electroanalytical device to give individual electrodes within the array. FIG. 6F shows such an arrangement. Reference to a "continuous 3D surface" in this context is intended to include such options (i.e. there may be a plurality of continuous 3D surfaces within the array structure).

Gold, as a choice of coating layer 3 (continuous 3D surface), achieves all of these roles. In some embodiments of the present invention, the coating layer 3 may also need to be transparent. Again, gold is capable of being transparent. A person skilled in the art will readily understand that other conductive materials (for example, silver, platinum and conducting polymers such as polypyrrole and polythiophene) will also be capable of achieving the above identified roles. Likewise, non-conductive materials (for example, graphene and carbon nanotubes) will at least be capable of achieving the majority of the above identified roles of the continuous 3D surface.

As indicated above, gold is the preferred coating material for use as a continuous 3D surface in the present invention because it is highly conductive (and therefore capable of acting as an electrode), is inert, forms a strong covalent bond with sulphur, is easy to deposit on the substrate material, has a well known chemistry and it is readily available. It is also able to withstand harsh chemical cleaning treatments which in turn ensures that the arrays of the present invention can be used more than once.

As used herein, "inert material" refers to a flexible or rigid material which physically isolates individual functionalisable areas from each other. Thus, the inert material forms an "inert surface" through, or from, which the functionalisable areas protrude or are otherwise exposed, therefore exposing isolated areas of the continuous 3D surface (coating layer 3) and thus allowing those areas to be functionalised as desired. In this arrangement, the array remains as a 3D array. Alternatively, the functionalisable areas do not protrude but align with the inert material surface to form a 2D (two-dimensional, i.e. flat) surface including functionalisable areas.

Suitable inert materials for use in the present invention include, but are not limited to, epoxy, spray-coatable materials such as paint, silicon dioxide, or photoresist materials such as SU-8. Epoxy or photoresist materials are typically used where flexibility is not required. The inert material may also be formed from a solid film or a monolayer of thiol terminated molecules, or a self-assembled monolayer (SAM) which are well known in the laser field. SAM's include an alkyl chain which is usually terminated by an —SH functional group at one end but may also be terminated by a variety of other functional groups, including but not limited to, —$CH_3$, —OH, —COOH, —$NH_2$, —CN, and —CHO. The choice of functional group depends on the target species to be bound to the microarrays of the present invention. The inert material may also act as an insulating material, and may also be seen to be a filler material or an isolation layer.

Depending on the inert material to be used in the present invention, its application may involve spin-coating the coating layer 3 of the microarray to a known thickness. Where this method of application is employed, the inert material is then cross-linked under ultra-violet light and individual functional areas are exposed by etching back the inert material by reactive ion etching. Numerous alternative methods for applying the inert layer would be known to those skilled in the art and include, but are not limited to, spray-coating followed by physical removal of the inert material from areas to be functionalised (for example, by wiping the tips), spray-coating a dilute coating material onto the coating layer 3 which upon application will flow off the tips and into the valleys of the 3D array, and dip coating a SAM monolayer followed by physical removal of the SAM on the tips.

The microarray of the first aspect of the present invention may be functionalised to be a micro-electrode sensor (as indicated above). It may also function as a microcatalyst array. Further discussion on the potential uses of the arrays of the present invention are discussed below.

In one embodiment of the first aspect, the present invention provides an accurately defined and functionalisable array, including a continuous 3D surface layer, formed from an intermediate structure 4. Again, individual functionalisable areas of the array are separated by a layer of the inert material to give an inert surface through, or from, which the functionalisable areas protrude or are otherwise exposed and the individual functionalisable areas are interconnected by the continuous 3D surface. Preferably, the individual functionalisable areas are conductively interconnected by the continuous 3D surface. The intermediate structure forms the base of the array.

Thus, in a second aspect, the present invention provides an intermediate structure 4 for use in fabricating an accurately defined, functionalisable array according to the first aspect of the invention. The intermediate structure is formed from a substrate material layer 2 that includes an accurately defined 3D pattern to a millimeter to nanometer scale. All or part of the 3D pattern is coated with a coating layer 3 to form a continuous 3D surface layer on the substrate material layer 2 that is capable of functionalisation for use as an array. It is preferred that substantially all the patterned area is covered with the coating layer 3 (continuous 3D surface). Optionally, the intermediate structure 4 will include an adhesion layer between the coating layer 3 (continuous 3D surface) and the substrate material 2.

Optionally, the intermediate structure 4 will include an adhesion layer between the coating layer 3 and the substrate material 2.

Figure 2:
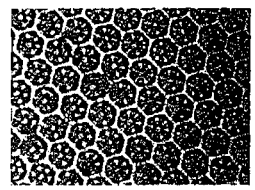
FIG. 2: (A) shows a 50 micron gold coated structure; (B) shows a 10 micron gold coated structure.
Figure 2:
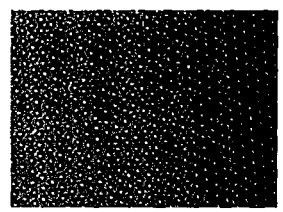

FIG. 1C shows an intermediate structure 4 of the second aspect of the present invention. FIG. 2A shows a 50 micron gold coated patterned substrate material while FIG. 2B shows a 10 micro gold coated patterned substrate material according to the present invention. Both are "intermediate" structures 4.

The intermediate structure 4 can be fabricated separately to the arrays in large continuous sheets thus providing economies of scale to the user. These large continuous sheets of coated and patterned material include accurately defined 3D patterns (of any desired type—lines, arcs, random) on the millimeter to the nanometer (inclusive) scale. Thus, in a third aspect, the present invention provides a method for the formation of an intermediate structure according to the first aspect of the invention, including a continuous 3D surface layer from which an array having accurately defined and functionalisable isolated areas can be formed, the method involving the steps of:
a. placing an accurately defined 3D pattern at the millimeter to nanometer scale on the surface of a substrate material; and
b. coating at least part of the patterned substrate material with a continuous 3D single coating layer.

Preferably, the coating layer 3 covers substantially all of the patterned area of the substrate material to form a continuous 3D surface layer.

Optionally, the method includes the step of adding an adhesion layer between the substrate material 2 and the coating layer 3.

The substrate material of the intermediate structure 4 (as depicted in FIG. 1C) is preferably formed from an inert polymer material. However, as indicated above, there are a number of other suitable flexible and non-flexible materials which may be used including thermoplastic polyurethane, rubber, silicon rubber, epoxy, PMMA, PC, PS, ceramic, resin and composite materials. Suitable techniques for placing an accurately defined 3D pattern at the millimeter to nanometer scale on the surface of the substrate material are described above and include embossing, casting, stamping, etching, grinding, lithography, pressure forming, vacuum forming, roll forming, injection moulding and laser scribing/ablation techniques.

Figure 7:
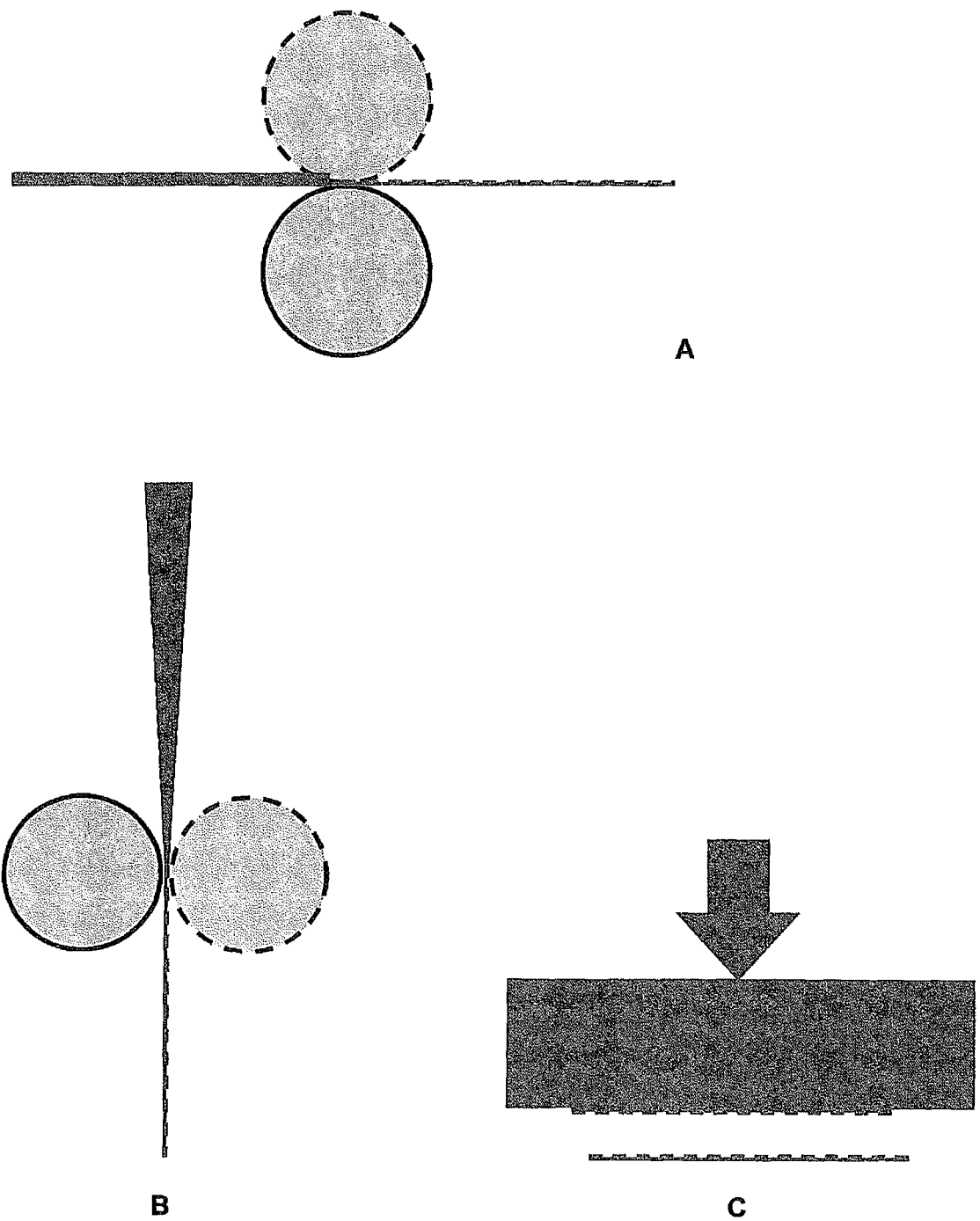
FIG. 7: shows, in schematic form, (A) roller embossing of a substrate material (for example, a polymer or glass substrate material); (B) roller embossing of a substrate material; and (C) embossing a substrate material using a stamp.

Alternatively, the intermediate structure 4 (as depicted in FIG. 1C) could be formed from a single layer of metal such as gold, silver, nickel or the like, depending on shape, size and cost restraints. The metal surface could then be embossed (or otherwise patterned) with a desired 3D pattern. Again, suitable techniques for forming the metal surface with a desired pattern are as described above and could include casting, stamping (FIG. 7C), etching, grinding, lithography, pressure forming, vacuum forming, roll forming (FIGS. 7A and 7B). Other suitable methods would be known to those skilled in the art.

The intermediate structure 4 of the second aspect can be used to form arrays of the present invention in one of three ways. In the first method, individual spaces 5 between functionalisable areas (depicted in the form of tips) 6 in the 3D pattern on intermediate structure 4 (FIG. 3C) are filled with an inert material 7. When used in this manner, the inert material essentially acts as a filler material or an isolation layer (FIG. 3F) to give an inert surface 8 through which the functionalisable areas or tips 6 of the intermediate structure 4 protrude or are exposed. FIG. 3F depicts the use of a solid film as the inert material 7. The functionalisable areas or tips 6 are thus isolated from each other and are capable of being functionalised as desired. Thus, once functionalised, they become functional areas (e.g. sensor sites) in an array form. FIG. 3G shows a diagrammatic top view of the functionalisable array of FIG. 3F. The functionalisable areas or tips 6 remain connected to each other by the coating layer 3 (continuous 3D surface) of the intermediate structure 4. However, not all of the coating layer 3 of intermediate structure 4 needs to be covered by the inert material 7. Those areas of the coating layer 3 which are not covered are then available for use in making electrical connection to the tips 6.

Therefore, in a fourth aspect, the present invention provides a method for the formation of a structure capable of functionalisation as an array according to the first aspect of the invention, the method including the steps of taking the intermediate structure 4 according to the second aspect of the invention and filling individual spaces 5 between the tips 6 of the 3D pattern on the intermediate structure 4 with an inert material 7 to give an inert surface 8 through which the tips 6 protrude or are otherwise exposed, said tips 6 forming functionalisable areas. Thus an array including a continuous 3D surface layer with isolated but interconnected, preferably conductively interconnected, functionalisable areas in an accurately defined pattern is formed.

Optionally, where the functionalisable areas protrude, the tips 6 of the protruding areas can be cut away to align with the surface 8 of the inert material 7 to form a 2D surface including isolated but interconnected functionalisable areas. Optionally, a portion of the inert material is also removed.

Alternatively, in the second method the inert material 7 can be added in sufficient amount to cover the functionalisable areas or tips 6 of the 3D pattern on the intermediate structure 4. The inert material 7 is then partially removed (by etching, abrasion, chemical or plasma techniques) to expose the functionalisable areas or tips 6 of the 3D pattern on the intermediate structure 4. This method provides a means of obtaining a 2D surface, as the functionalisable areas or tips 6 do not protrude above the inert material 7. The exposed functionalisable areas or tips 6 are isolated from each other by the inert material 7 but remain interconnected, preferably conductively interconnected, within the structure by coating layer 3 of the intermediate structure 4.

Therefore, in a fifth aspect, the present invention provides a method for the formation of a 2D microarray structure of the present invention, the method including the steps of taking the intermediate structure 4 and covering the 3D pattern on the intermediate structure 4 with an inert material 7, and removing sufficient of the inert material 7 to only expose the functionalisable areas or tips 6 of the 3D pattern.

The array formed by either of the above methods includes an intermediate structure 4 formed from a substrate material 2 (which is inert) and 3D patterned to a millimeter to nanometer scale, a coating layer 3 over at least part of the patterned area to form a continuous 3D surface, and a layer of inert material 7 which is layered over the continuous 3D surface and fills spaces 5 between functionalisable areas or tips 6 in the 3D pattern on the intermediate structure 4 to give an inert surface 8 through, or from, which the functionalisable areas or tips 6 of the 3D pattern protrude or are otherwise exposed. As indicated above, the functionalisable areas or tips 6 are isolated by the inert material 7 but are continuously interconnected via the coating layer 3 (continuous 3D surface) which is present over at least part of the 3D patterned area (preferably substantially all of the patterned area).

Figure 4:
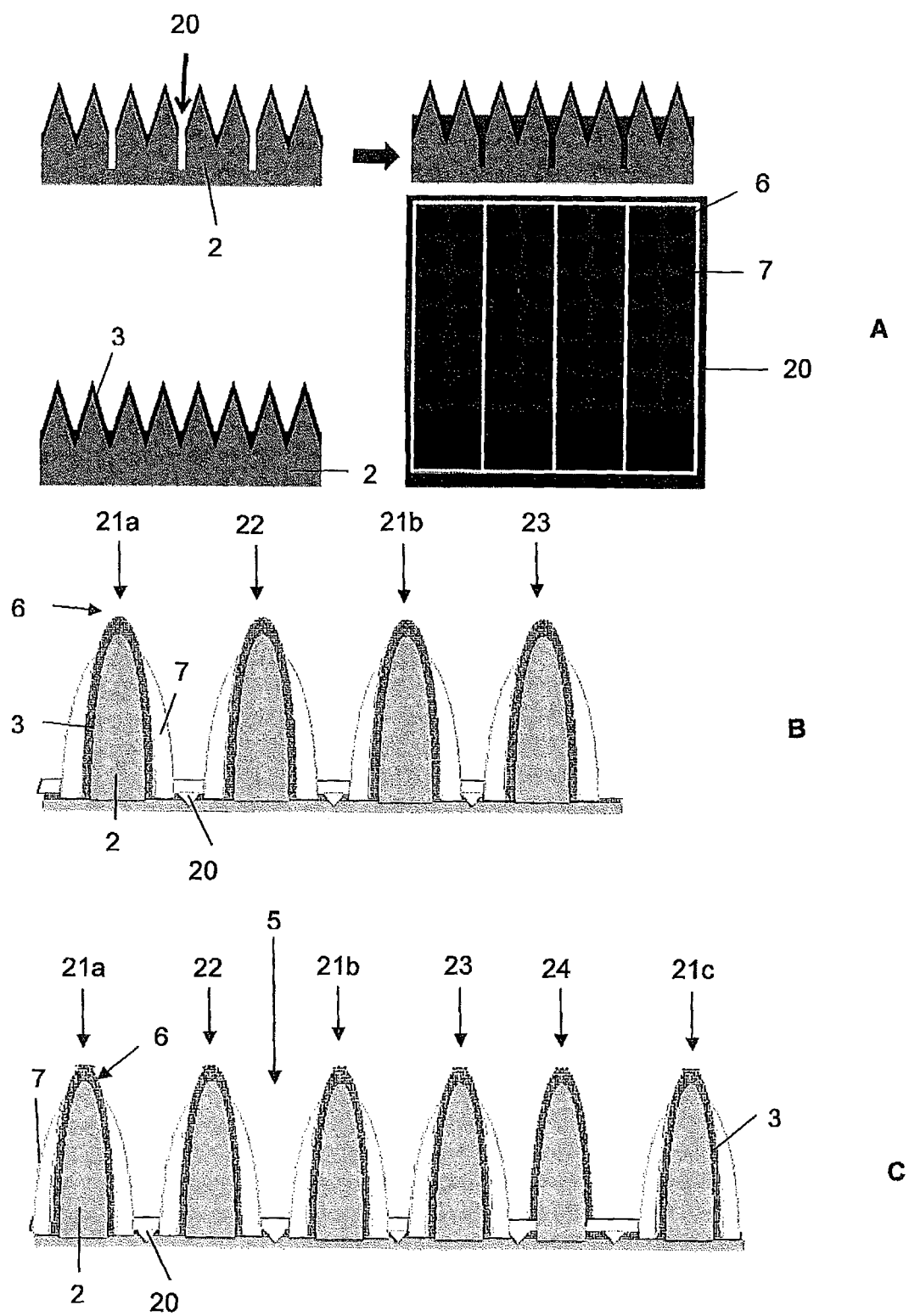
FIG. 4: (A) shows, in schematic form, the use of a laser to scribe lines in the coating layer in between the tips to produce four isolated micro-electrode arrays (IV) on the same sensor chip (A, B, C and D). The four isolated micro-electrode arrays can be configured in a number of ways as shown in (B) and (C), each of which show a cross-section of a micro-electrode array spanning across electrically isolated rows of tips.

As shown in FIG. 4A, electrically isolated groups of arrays can also be formed using the above methods in combination with a process of laser scribing, wherein the coating layer 3 (continuous 3D surface) between individual functionalisable areas or tips 6 is etched out (as depicted by 20 in FIGS. 4B and C, FIGS. 5A and B and FIG. 6F). This allows a single sensor chip to have individually addressable areas which could include a counter electrode(s), a reference electrode(s), a redox electrode(s) and working electrode(s). There is no restriction to the shape of the lasered lines. However, it is preferable that the width of the lasered lines is between about 1 to about 100 micron. The individually addressable areas or isolated micro-electrode arrays can be configured in a number of ways, two examples of which are shown in FIGS. 4B and 4C. In FIG. 4B, the micro-electrode array includes two working electrodes 21a and 21b, separated by a counter electrode 22, and a reference electrode 23. In FIG. 4C, the micro-electrode array includes three working electrodes (21a, 21b and 21c), a counter electrode 22, a reference electrode 23 and a redox electrode 24, wherein the counter electrode separates working electrodes 21a and 21b and the reference electrode 23 and redox electrode 24 together separate working electrodes 21b and 21c. The isolated micro-electrode arrays may also be arranged such that each functions as a working electrode 21.

In the third method, the coating layer 3 (FIG. 3C) acts as a seed layer. The intermediate structure 4 is placed into an electroplating bath to electrochemically grow the coating layer 3 (continuous 3D surface). It is therefore preferable that the coating layer 3 (continuous 3D surface) is electrically conductive and the metal employed is capable of being electrochemically deposited onto the coating layer 3 (continuous 3D surface) where this method is employed. The coating layer 3 (continuous 3D surface) is electrochemically grown to form a metal layer 9 that at least substantially covers the functionalisable areas or tips 6 of the intermediate structure 4 (FIG. 3D). The metal layer 9, which includes, and therefore incorporates, the coating layer 3 of intermediate structure 4, is then separated from the remainder of the structure 4 to give a metal negative 3D pattern 10 (a negative of the pattern on structure 4 (FIG. 3E)). Individual spaces 11 between the functionalisable areas or tips 12 in the negative 3D pattern on the metal negative 10 are then backfilled with an inert material 7 to give a flat surface 8 through, or from, which the tips 12 of the metal negative 10 protrude or are otherwise exposed (FIGS. 3H and 3G). Again, when used in this manner, the inert material 7 essentially acts as a filler material or an isolation layer. Also, where the tips 12 protrude from the inert material 7, they may be cut away to align with the surface 8 of the inert material 7 to form a 2D surface including isolated but interconnected functionalisable areas. The functionalisable areas or tips 12 are isolated by the inert material 7 and are capable of being functionalised as desired to form functional areas (e.g. sensor or catalytic sites) in an array form.

Thus, in a sixth aspect, the present invention a method for the formation of an array which includes a continuous 3D surface layer with an accurately defined 3D pattern of functionalisable areas in the millimeter to nanometer scale, said method including the steps of:
  a. electroplating the continuous 3D surface layer of the intermediate structure 4 to form a metal layer 9 that covers the tips 12 of the 3D pattern (preferably at least substantially all of the 3D pattern) on the intermediate structure 4;
  b. separating the metal layer 9 and the substrate material 2 of the intermediate structure 4 to form a metal negative structure 10 which includes a negative of the 3D pattern ("negative 3D pattern") on the intermediate structure 4;
  c. backfilling spaces 11 between tips 12 within the negative 3D pattern on the metal negative structure 10 with an inert material 7 to give an inert surface 8 through, or from, which the tips 12 of the negative 3D pattern protrude or are otherwise exposed.

Any metal can be employed in the electroplating step to form the metal layer 9. The use of Nickel is preferred as it is a hard and ductile metal and is commonly used as a plating metal.

FIG. 3G shows a diagrammatic top view of the functionalisable array formed by the filling of individual spaces 11 between functionalisable areas or tips 12 in the negative pattern on the metal negative 10 (FIG. 3H). Thus, the metal negative 10 acts as the substrate material layer of a microarray structure. The present invention may therefore extend to a functionalisable array when formed by the method of the sixth aspect of the present invention.

Therefore, the present invention also provides a microarray with a conductive base which is capable of being coated with a continuous 3D surface (conductive or non-conductive) and/or an inert material 7 to form isolated functionalisable areas.

As will be appreciated, the methods described above for using the intermediate structure 4 (FIG. 3C) result in an array having the same top view shown in FIG. 3G.

The ability to create accurately defined arrays at the millimeter to nanometer scale has been an issue in the array field for some time. The small sizes at issue, particularly in the nanometer scale, present particular problems when seeking to obtain accurate quantitative and/or qualitative analyses. The present invention provides an economic approach to the creation of such arrays.

Figure 6:
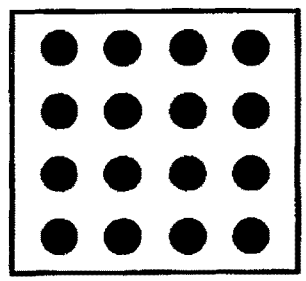
FIG. 6: shows the typical types of micro-electrode arrays. (A) shows a microdisk electrode array (could be ordered or random); (B) shows a microband electrode array; (C) shows an inter-digitated micro-electrode array (planar and vertical); (D) shows a linear micro-electrode array; (E) shows a 3D micro-electrode array; and (F) shows electrically isolated individual tips with electrical connections from each tip.
Figure 6:
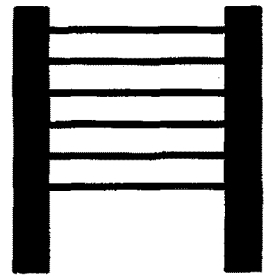
Figure 6:
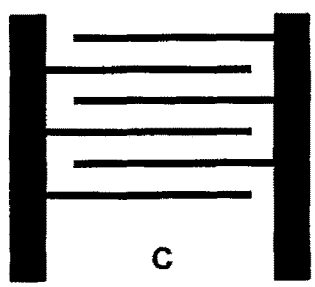
Figure 6:
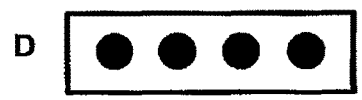
Figure 6:
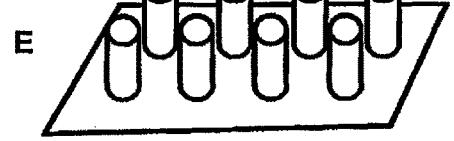
Figure 6:
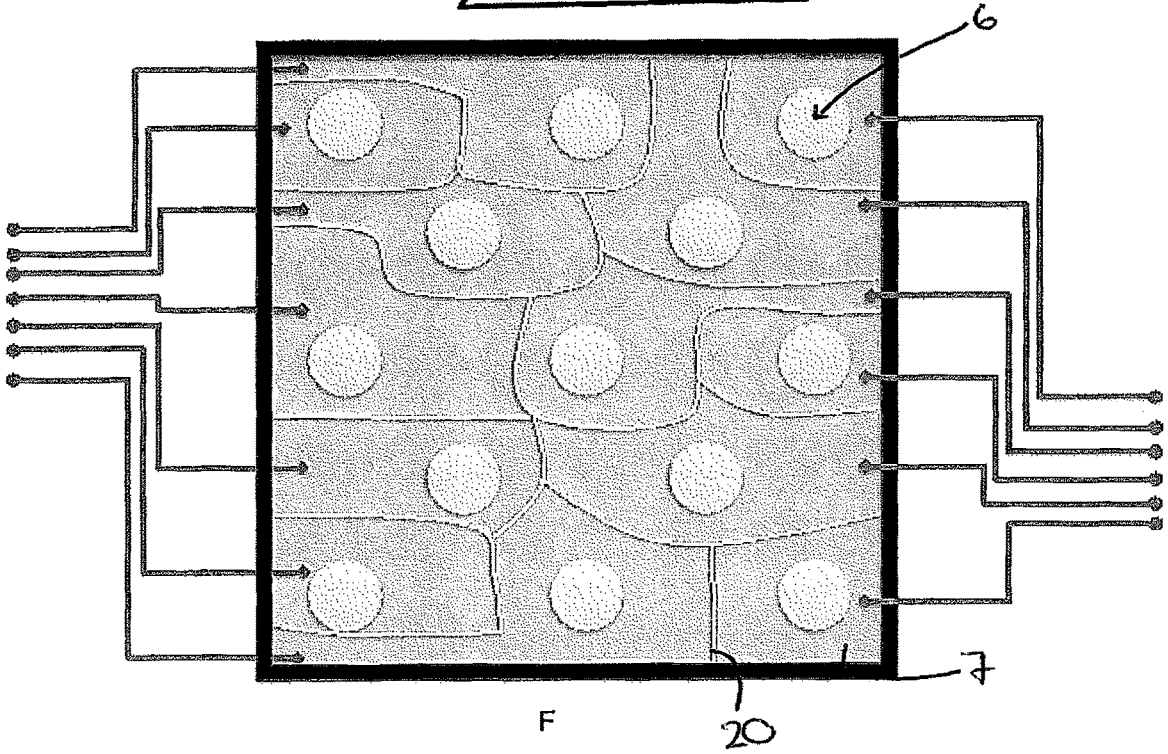

As is clear from FIGS. 3F and 3H and as discussed above, the isolated functionalisable areas (formed by tips 6 and 12) in the array are interconnected below the inert material 7 via a continuous 3D surface (i.e. coating layer 3 or metal negative pattern 10). Where the continuous 3D surface is formed from a conductive material (for example, gold), the isolated functionalisable areas are conductively interconnected with each other as discussed above and therefore act as interconnected but isolated conductive islands. Also, as indicated above, the continuous 3D surface can be laser scribed or otherwise cut into individual sections such that individually isolated blocks of functionalisable areas are formed within a wider array structure. The use of a conductive material allows the arrays formed by the methods of the present invention to be functionalised to form micro-electrode arrays as discussed above. Therefore, the entire array can act as a single micro-electrode. Alternatively, the array can include multiple individual electrodes where the continuous 3D surface has been cut into isolated blocks. The interconnection also allows efficiencies of charge functionalisation of the isolated sites in the micro-electrode array. Micro-electrode arrays can be of a variety of types as shown in FIG. 6, including:

microdisk electrode arrays, on which the arrays may be arranged in a ordered or random fashion;
microband electro arrays;
inter-digitated microelectrode arrays, which may be planar or vertical;
linear microelectrode arrays; and
3D microelectrode arrays.

When functioning as a micro-electrode array, the continuous 3D surface is connected to an electroanalytical device, electrical contact is made with an electrolytic solution and current is allowed to flow through the solution. Target species in the electrolytic solution bind to the functionalised areas of the microarray and therefore aid or impede current flow. In this way, the target species are "sensed" by the micro-electrode array. Capture agents that are specific to the target species can also be appended to the functionalisable areas of the micro-electrode array to aid in this interaction. Individual micro-electrode arrays may also be used as counter-electrodes to each other, whereby a current is passed between individual functionalised areas on each and the current is measured.

The electrical communication achieved by use of a conducting continuous 3D surface (coating layer 3) also allows the arrays of the present invention to provide insight into the redox environment of a sample passing over the surface of the array. For example, the arrays can be used to ascertain whether the redox environment of the sample is oxidative or reductive (therefore allowing for the establishment of the likes of anti-oxidant response elements), or whether there are peroxides present or radicals present.

The use of techniques such as laser scribing or lithography to cut the continuous 3D surface (coating layer 3) into individual isolated blocks or areas also imparts on the microarrays of the present invention the ability to function as multiplexing arrays, wherein simultaneous testing or measurement of multiple analytes or biomarkers can be conducted (FIG. 6F). Such a system could be used to detect known biomarkers relevant to a specific disease, organ or system. This also allows the user to isolate a known number of sensor sites for different purposes.

Where the user wishes to create non-conducting (or otherwise non-functionalised) isolated areas, a non-conductive coating material 3 can be employed or the metal negative 10 can be coated with a non-conducting layer.

The isolated functionalisable areas (identified at 6/12 in FIG. 3G) can also be used in a number of other array applications. For example, they may be functionalised to act as catalysts in a variety of micro reactions, or to act as sensors for various target biomolecules or compounds of interest. Other suitable uses will be known to those skilled in the art. The means to functionalise the areas would also be well known to a skilled person once in possession of this invention.

Thus the present invention provides a structure including a continuous 3D surface which is capable of functionalisation for use as an array, the structure including accurately defined and functionalisable isolated areas which are millimeter to nanometer in size. The functionalisable areas are isolated by an inert material 7 (which may also act as an insulator) but are continuously interconnected within the structure. Preferably, the functionalisable areas are continuously interconnected by a 3D coating layer 3 within the structure. Preferably, the functionalisable areas are electrically conductive.

The present invention also provides an intermediate structure 4 including a continuous 3D surface capable of functionalisation for use as an array, wherein the intermediate structure 4 includes an accurately defined 3D pattern at the millimeter to nanometer scale on at least one surface. The intermediate structure 4 also includes an inert material 7 between the tips 6 of the 3D pattern which creates a surface 8 through which the tips 6 of the 3D pattern protrudes or are otherwise exposed, the tips 6 of the 3D pattern thus being isolated by the inert material 7 and being interconnected within the intermediate structure 4 by the continuous 3D surface.

Reference to "accurately defined" means that the 3D pattern (or 2D pattern) includes a known, pre-determined (or calculatable) number of functionalisable areas in a known pattern. It is of course possible for the pattern to be randomised. Accuracy also includes the concept that the size and/or position of the functionalisable areas are pre-determined and accurately included in the structure.

As indicated above, the microarrays of the present invention are suitable for use as micro-electrode arrays, micro-catalyst arrays, and sensors for various target biomolecules or compounds of interest.

When a microarray of the present invention is used as a micro-electrode array (and therefore includes a conductive continuous 3D surface layer), the array would be functionalised by attaching a capture agent that is specific for the target analyte. Examples of suitable capture agents include small molecules, antibodies, and single stranded DNA. Other capture agents would be known to those skilled in the art. There are numerous methods for attaching the capture agent to an array. Methods of attachment typically include initial attachment of a linker molecule with a terminal carboxyl or amino group, onto which the capture agent is bound using standard binding methods, as would be known to those skilled in the art and are also discussed in related co-pending PCT application number PCT/2011/000052, the disclosure of which is included by way of reference. Suitable applications for the use of a micro-electrode array of the present invention include detection of small molecule bio-markers, proteins, DNA/RNA and organisms.

Electrical connection to a micro-electrode array of the present invention is typically achieved by attaching a clip or pressing a conductor (conductive paste, wire, ribbon) against the part of the electrode which is not in contact with the solution to be passed over the surface of the micro-electrode array.

When a microarray of the present invention is used as a microcatalyst array, it is essential that suitable binding chemistry is first attached to the functionalisable areas of the array. The attachment of suitable binding chemistry may be achieved in a number of ways including, electrochemical deposition of the binding chemistry where a conductive continuous 3D surface layer is used, and exposure of the functionalisable areas to suitable functional groups. Suitable functional groups may include a metal catalyst (for example, platinum or palladium), DNA, and conducting polymers such as polypyrrole and polythiophene. The different surfaces of the microcatalyst arrays so created react with the species in solution to a greater or lesser extent. The combination of responses allows the solution to be characterised electrochemically.

EXAMPLES

Example One: Computer Modelling of Micro-Electrode Sensors

Figure 8:
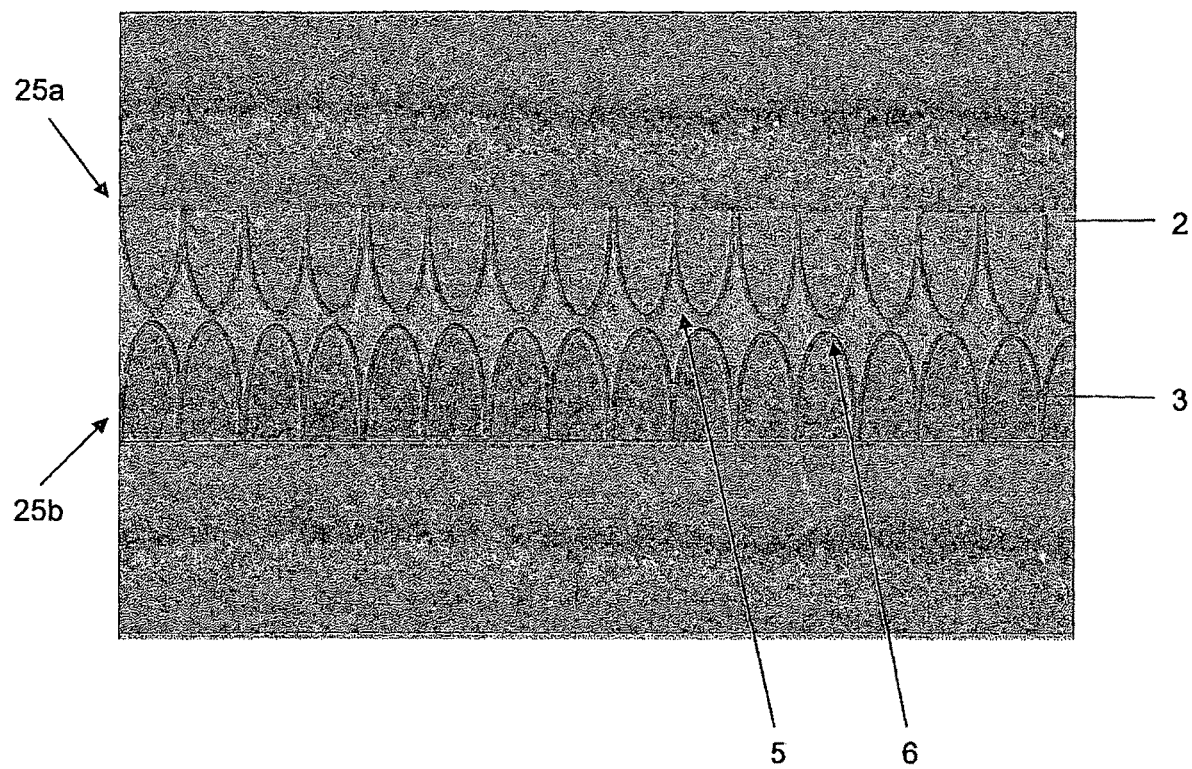
FIG. 8: shows the sensor design for computer modelling experiments in which two arrays of gold coated tips were precisely aligned over each other.

A series of computer modelling experiments were carried out on a single functionalisable area or tip of two individual micro-electrode arrays of the present invention, wherein the two micro-electrode arrays 25a and 25b were precisely aligned over each other as shown in FIG. 8. Thus, each micro-electrode array 25a and 25b was acting as a counter-electrode to the other.

The aim of these experiments was to calculate the impedance profile for different shapes and sizes of condensed droplets formed in between the tips. This was dependant on the concentration of the buffer solution and the size and shape of the droplet formed between the electrodes. The total impedance between two electrodes is the sum of the impedance at the electrode-electrolyte interface and the impedance of the electrolyte solution. In order to measure the impedance changes due to changes in the geometry of the system, the total impedance of the system was simulated by solving the modified Laplace's equation for two different geometries. The interface impedances were assumed to remain constant for different geometries and the interface reactions were not considered in the model.

Figure 9:
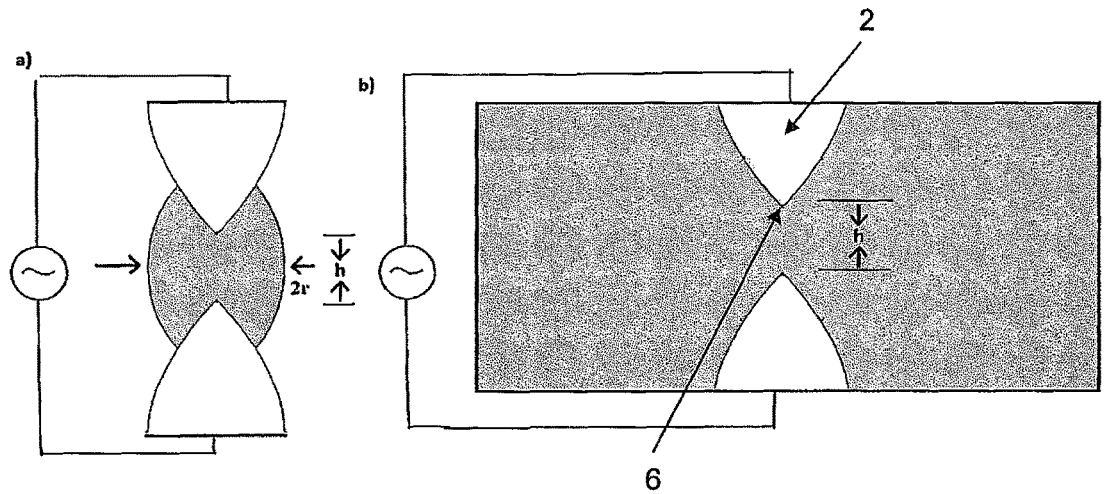
FIG. 9: shows two different geometries. (A) shows droplet formation and (B) shows a chamber filled with electrolyte showing potential distribution and current density vectors (arrows) in 2D and 3D domain.
Figure 9:
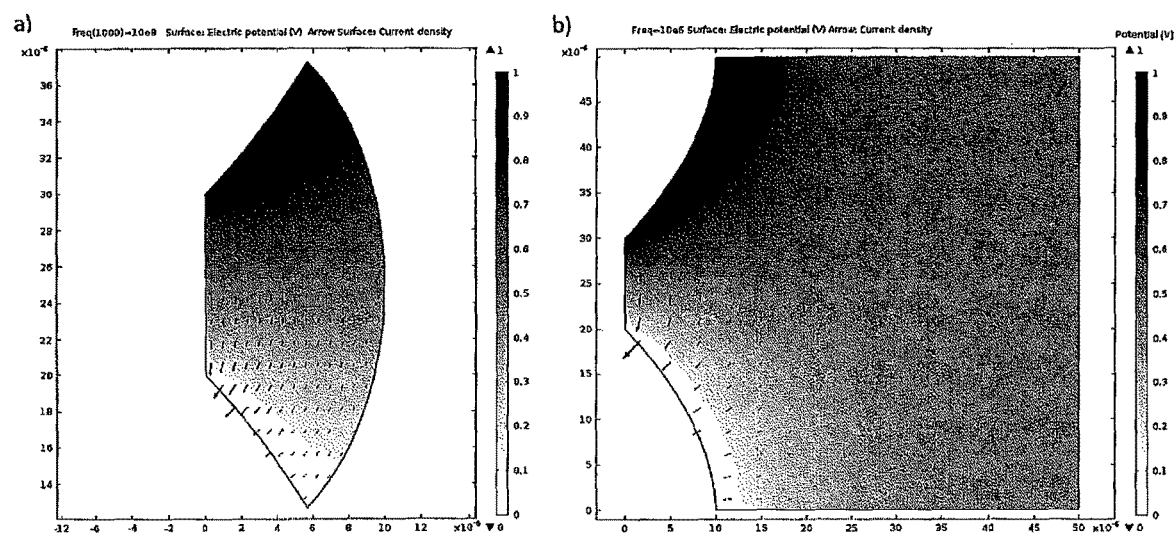
Figure 10:
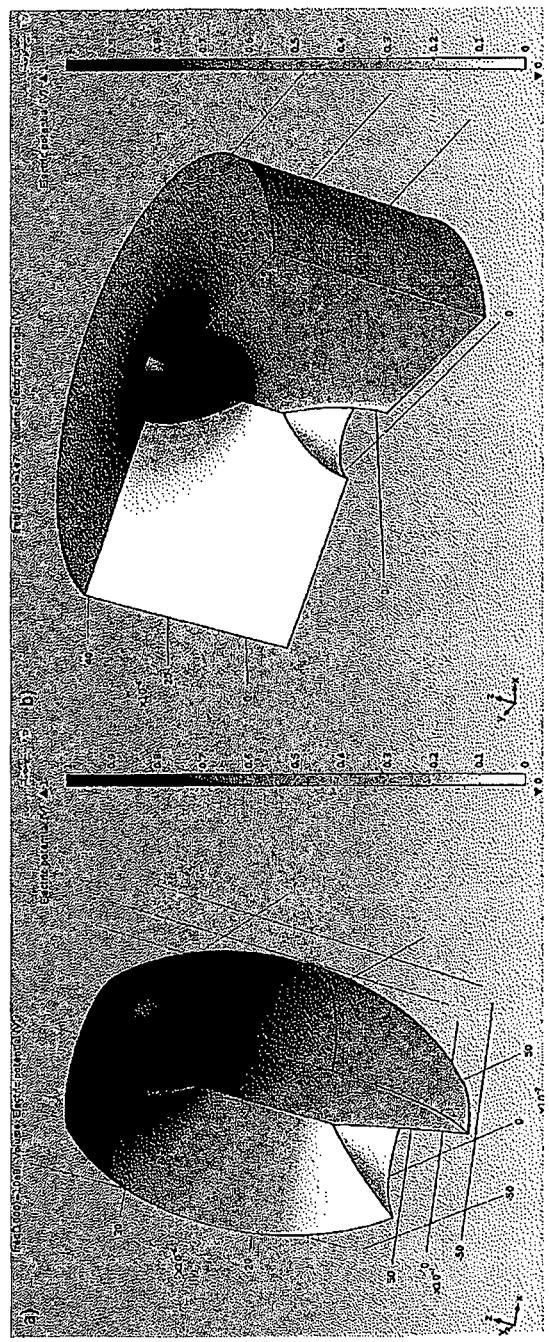
FIG. 10: shows a 3 dimensional rendering of impedance results.

An AC potential of 1 V was applied between the upper and lower electrodes and total impedance was calculated from the current distribution for a frequency range of 1 KHz to 1×106 KHz. The buffer was considered as a solution with conductivity of 0.02 S/m and a relative permittivity of 80. The results are illustrated in FIGS. 9 to 14 which model three parameters including the distance between the electrodes, the area of the electrodes, and the volume of the electrolyte (as either a droplet between the tips or as a solution that completely covers the tips). In summary, the results showed that sensitivity is inversely related to both the distance between the electrodes and the electrode area, but not significantly affected by the volume of the electrolyte at the micron scale. In FIG. 9, two different tip geometries are shown. In FIG. 9A droplet formation is shown while FIG. 9B shows a chamber filled with an electrolytic solution. Impedance results are shown by the potential distribution (FIGS. 9 and 10). The arrows indicate current density vectors in the 2D and 3D domain.

Figure 11:
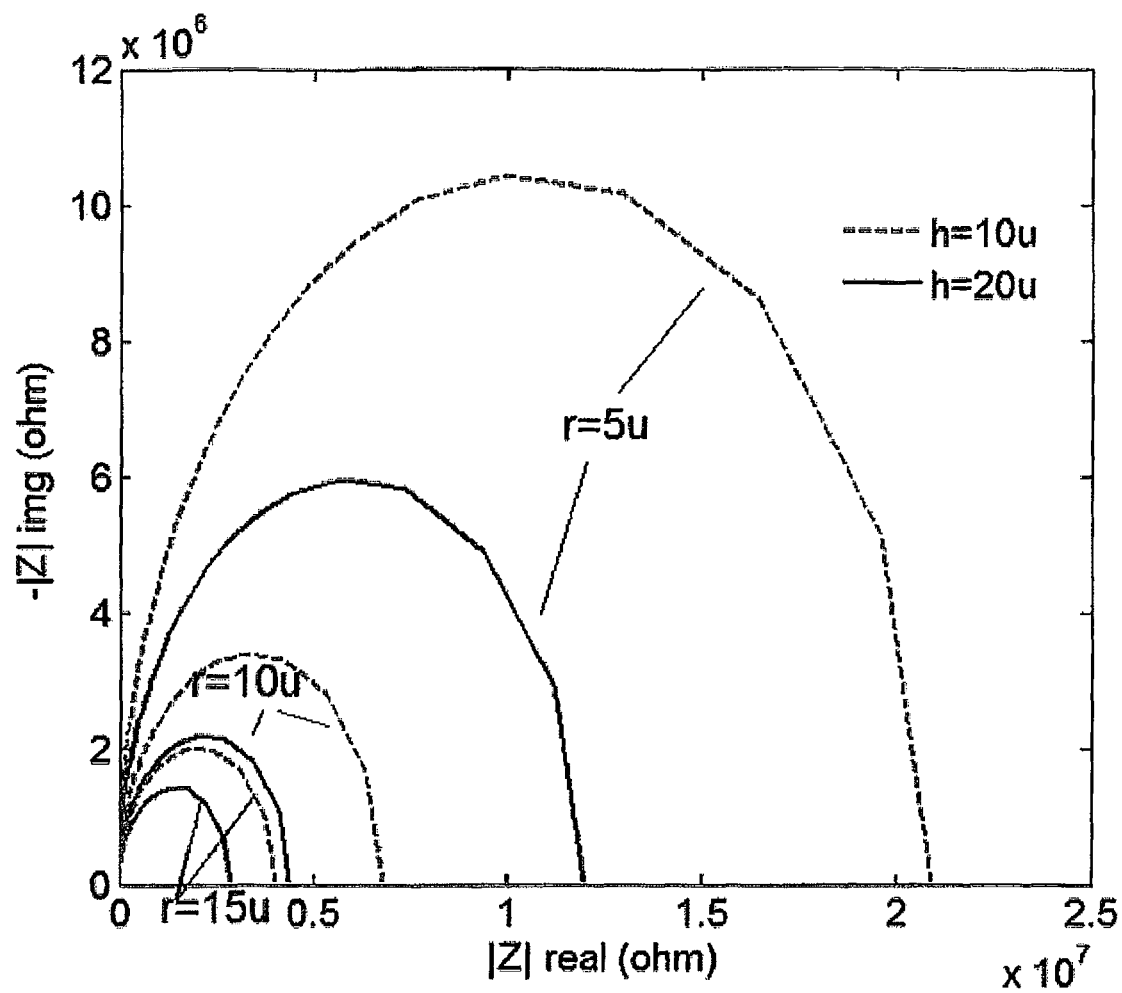
FIG. 11: shows impedance for various parameters of space between the 2 electrodes (10 and 20 micron), where r is the radius of the tip.
Figure 12:
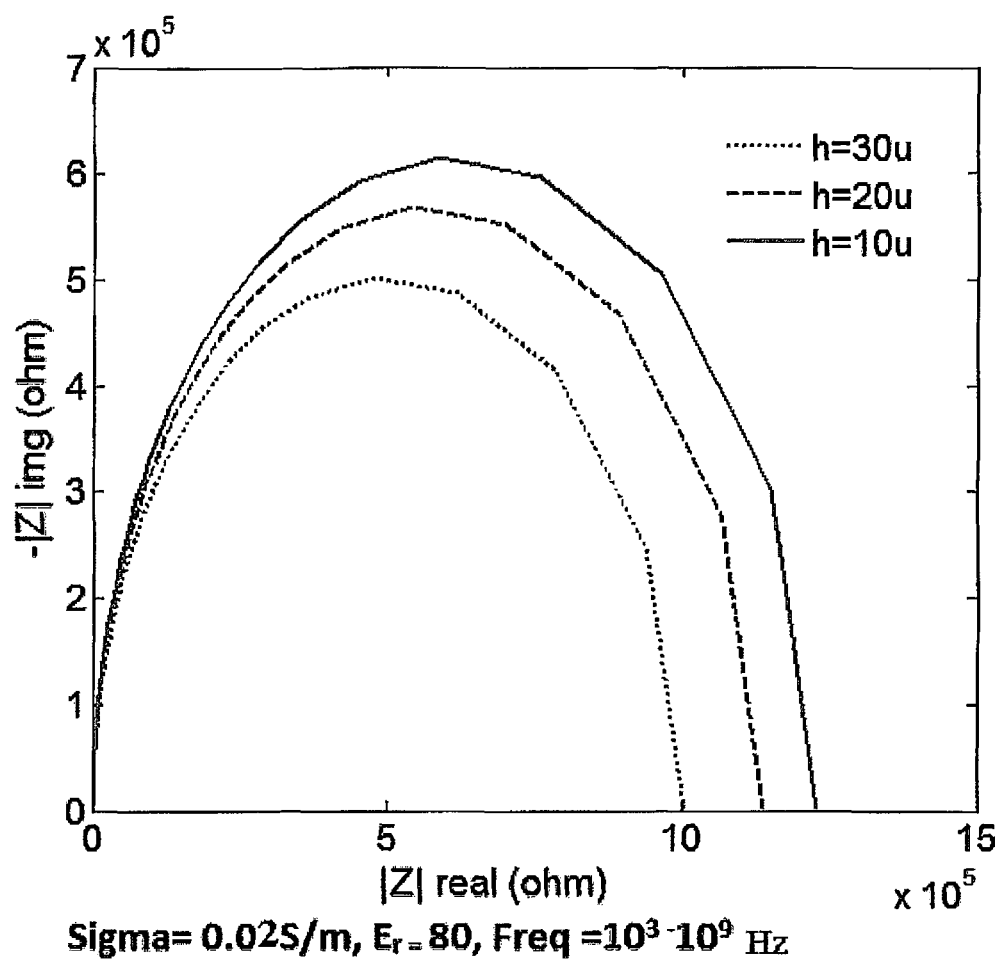
FIG. 12: shows impedance for various parameters of distance.
Figure 13:
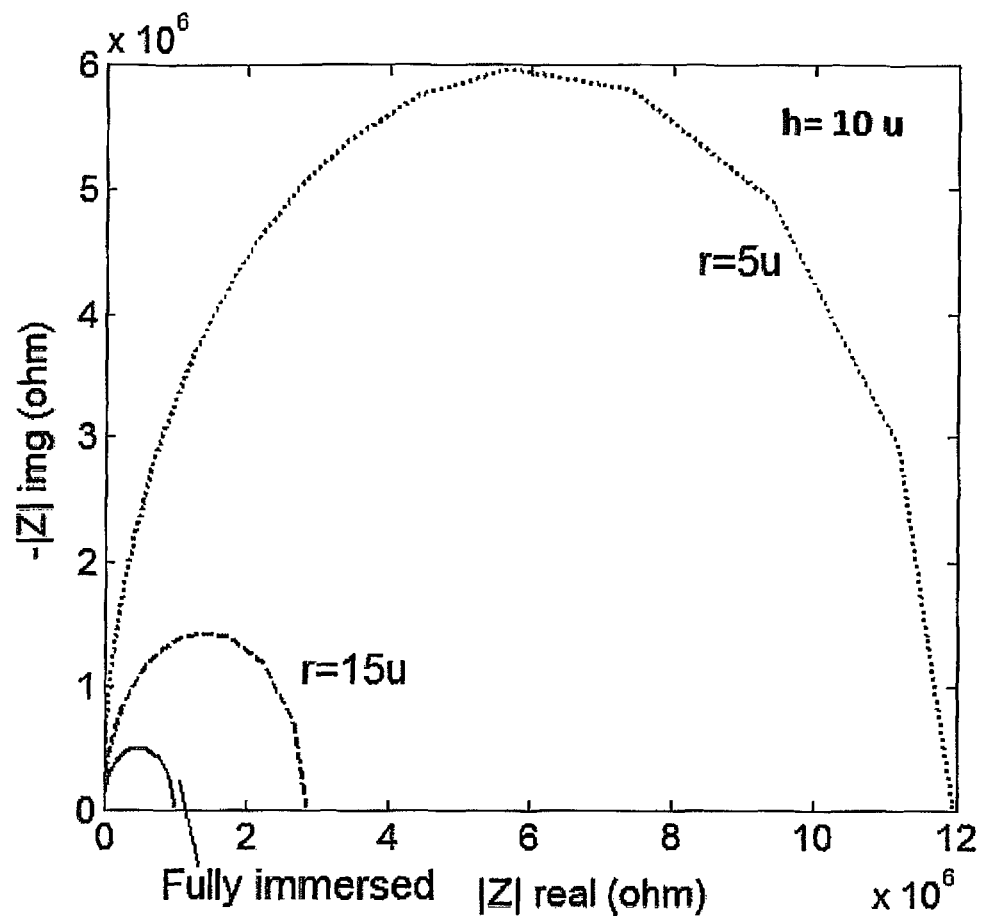
FIG. 13: shows impedance comparison between two distance geometries. Red shows fully immersed geometry. Green and blue show the droplet formation with different radius, geometry.
Figure 14:
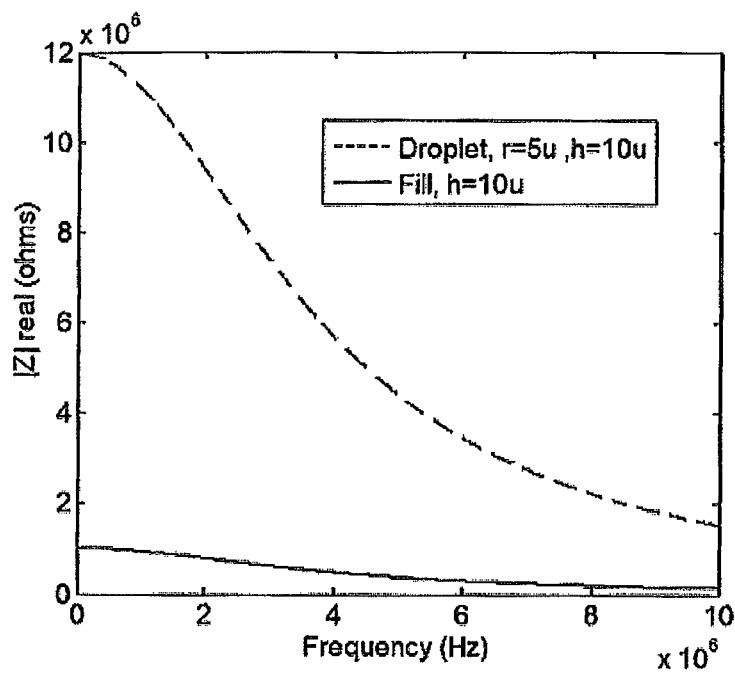
FIG. 14: shows Frequency vs. Impedance (Bode plot) for two different geometries, wherein the solid line shows geometry B, and the dotted line shows a droplet with radius 5 um.

FIGS. 11 to 13 show various impedance measurements, while FIG. 14 shows frequency vs. impedance for two different geometries.

Figure 15:
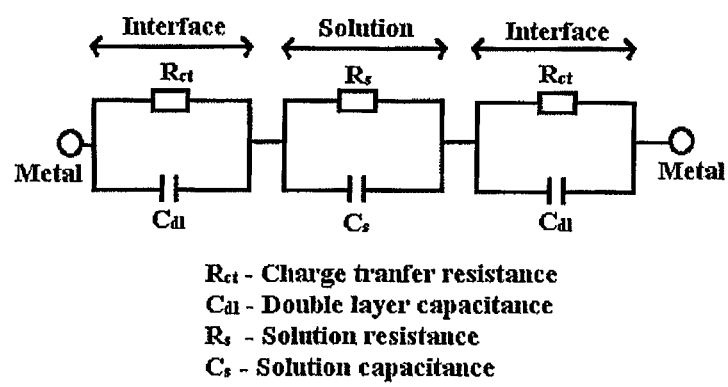
FIG. 15: shows an equivalent circuit model for the whole system including the interface impedance.
Figure 16:
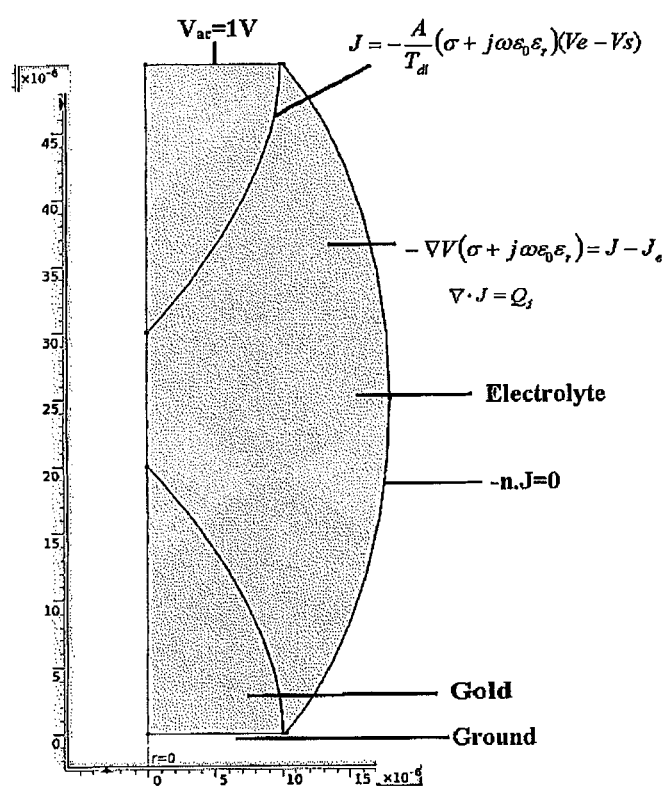
FIG. 16: shows model geometry along with domain equations and boundary conditions.

For bio-sensing applications, the electrodes were assumed to be functionalized with capture agents and then the impedance was measured before and after the capture. The change in the impedance was primarily due to changes at the electrode interface. The equivalent circuit model of the interface can be given by the Randle's circuit (neglecting the Warburg element due to diffusion of ions at the interface). The total equivalent circuit of the system with the interface and the solution impedance is illustrated in FIG. 15, and the domain equations and boundary conditions are shown in FIG. 16.

Figure 17:
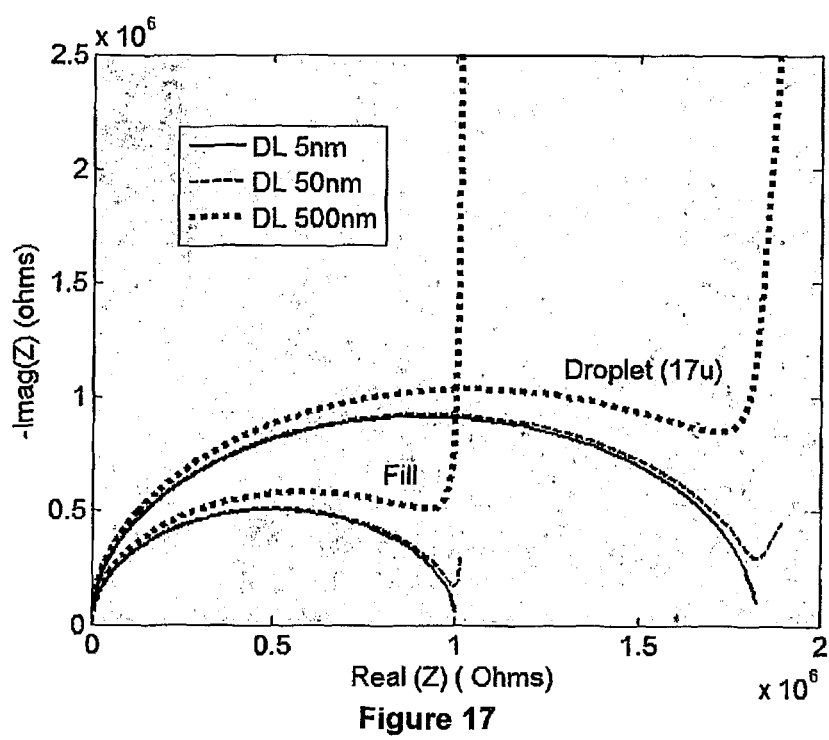
FIG. 17: shows impedance (Nyquist plot) for various double layer lengths of the interface for two different geometries.
Figure 18:
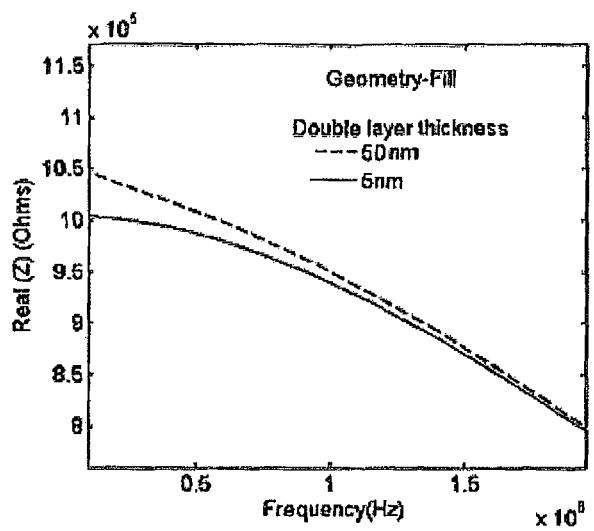
FIG. 18: shows a Bode plot showing difference in the Real Z (ohms) for two different double layer thickness.
Figure 19:
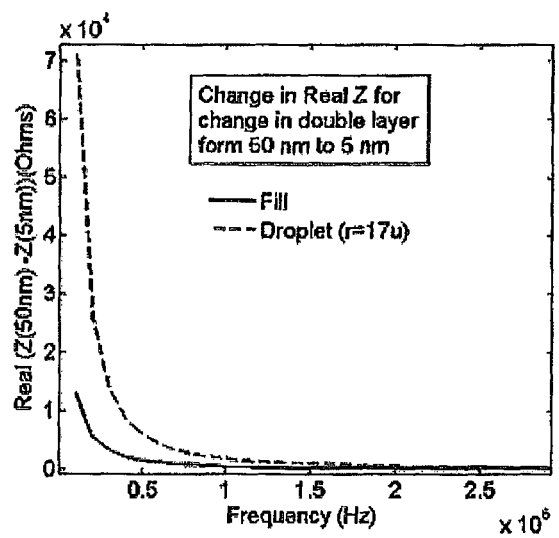
FIG. 19: shows difference between the impedance due to change in double layer from 50 nm to 5 nm for the two geometries.

Variations in double layer capacitance (the ability of a body to store an electric charge) are measured using Non-faradaic electrochemical impedance spectroscopy (EIS). This involves neglecting any changes due to redox reactions and measuring the capacitance changes due to changes in the double layer thickness. In order to determine the total impedance change of the system due to changes in double layer thickness, the model was simulated for various double layer thickness (Ddl) (FIGS. 17, 18 and 19). For all the cases charge transfer resistance (Rct) equates to 1M ohm. The results indicated that the droplet is only slightly more sensitive than using a completely submerged sensor tip.

Figure 20:
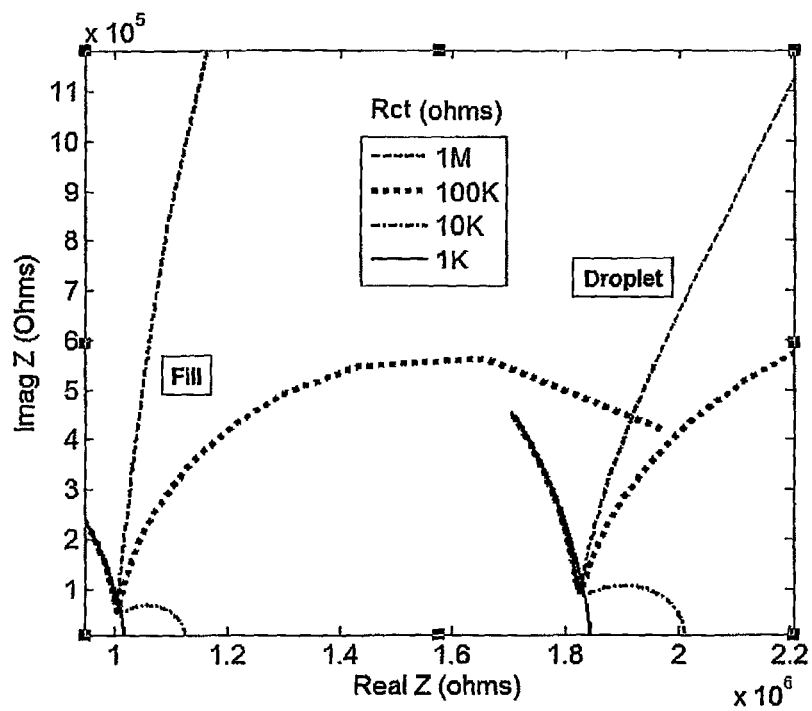
FIG. 20: shows the change in the impedance due to change in charge transfer resistance (Rct) for the two different geometries.
Figure 21:
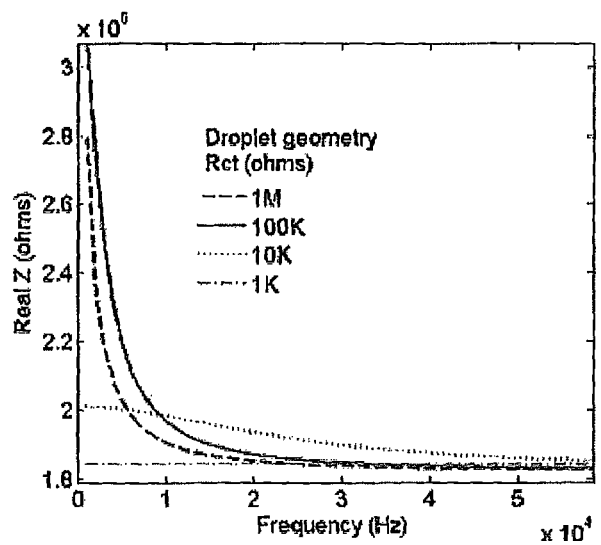
FIG. 21: shows change in the impedance due to change in Rct for the fill geometry.
Figure 22:
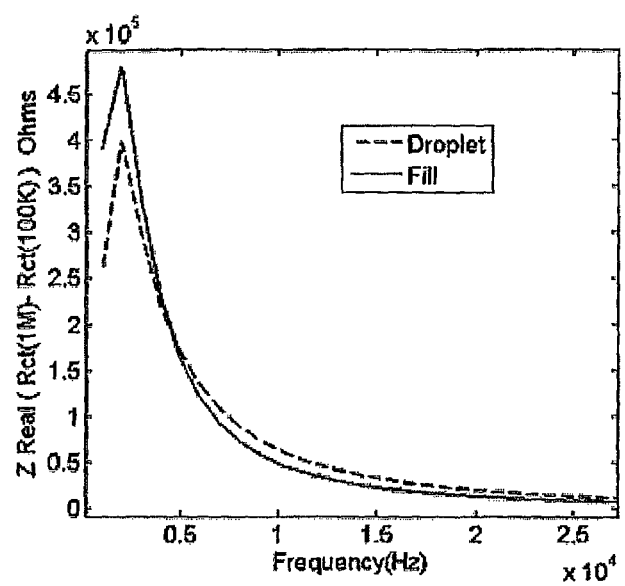
FIG. 22: shows difference between the impedance due to change in Rct from 1M ohm to 100K for the two geometries.

The second way to detect the changes at the interface is by measuring the redox reaction at the interface. When there is a change in the interface due to biological capture agents, the rate at which the redox reaction takes place changes. This changes the current at the interface, which consequently changes the Rct of the system. The Rct values vary for various different interfaces. Impedance changes of the system were simulated for various Rct. Results are illustrated in FIGS. 20, 21 and 22 and show that a droplet provides slightly better sensitivity at lower frequencies.

The computer modelling experiments showed that the smaller the dimensions of the tips, and the gaps between the tips, the greater the sensitivity of the sensor array.

Figure 34:
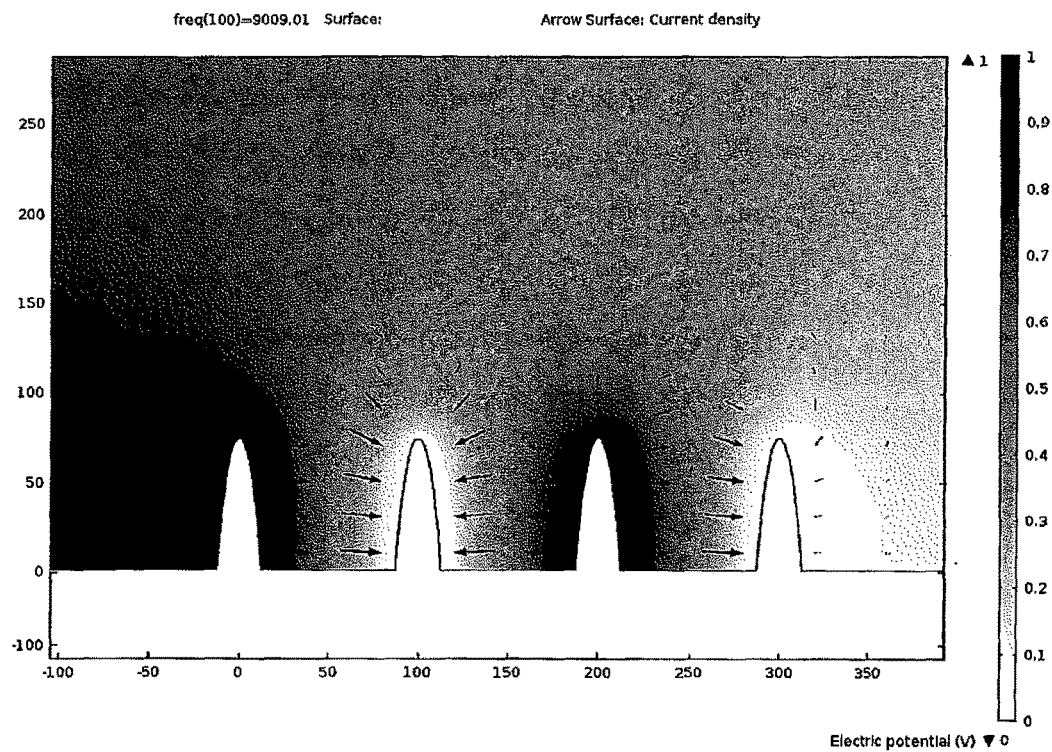
FIG. 34: shows potential distribution and current flow between inter-digitated electrode tips.

The design was also simplified to arrange working and counter electrodes side-by-side via inter-digitation patterning, thus enabling the different electrodes of an electrochemical set up (for example, working electrodes, counter electrode and reference electrode) to all be placed on the same micro-electrode array sensor chip. The electrochemical interactions of side-by-side electrode protrusions were modelled and similar results were observed to that of the micro-electrode array set up shown in FIG. 8. Therefore, in summary, impedance measurements relate to the distance between working and counter electrodes and the diameter of the working electrode (FIG. 34).

Example Two: Formation of Array Substrates, Intermediate Structures and Materials The above description describes different approaches to the formation of arrays of the present invention having isolated functionalisable areas or tips. In FIG. 3F a thin layer of an inert material 7 has been deposited over a continuous 3D metal surface to sit between individual tips of a 3D patterned substrate material 2. In FIG. 3H a thick layer of metal 9 has been deposited over and onto the continuous 3D surface of a substrate material 2. However, in both, functionalisation occurs predominately at the tips of the 3D pattern of the microarray.

The following describes the development of microarrays according to the fourth, fifth and sixth aspects of the present invention.

Figure 23:
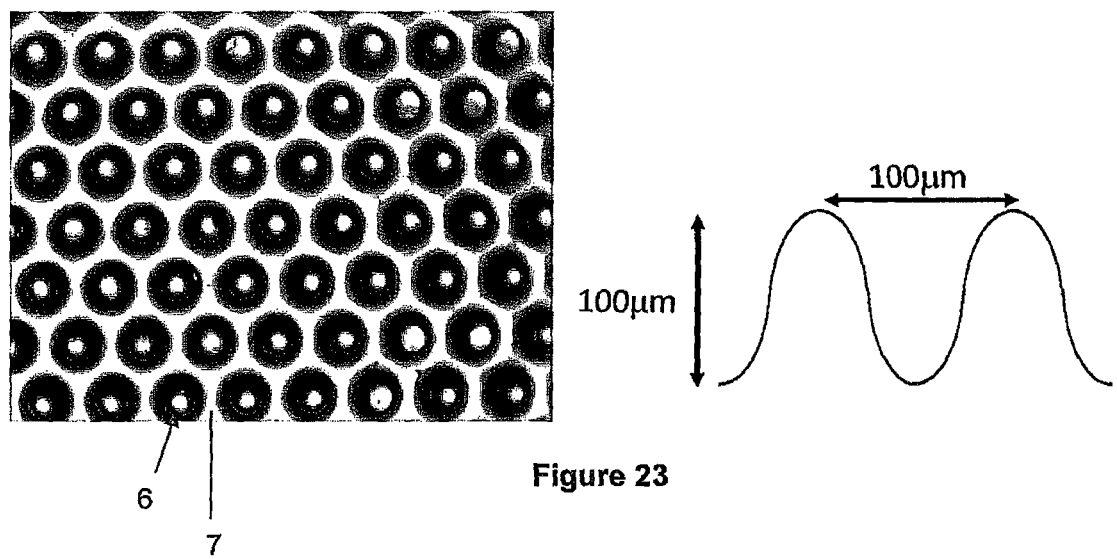
FIG. 23: shows a picture of 40 micron tips in PMMA.

Development of Arrays According to the Fourth and Fifth Aspects:

FIG. 23 shows a photograph of 40 micron tips embossed into PMMA and which are evenly spaced at 100 micron intervals and are 100 microns in height. PMMA (an amorphous polymer) is a preferred substrate material for use in the present invention as it is easily processed and gives highly defined three-dimensional substrate surfaces.

The process for fabricating the sensor (FIG. 24) includes the following steps:
1. Gold coating the substrate to form a continuous 3D gold surface (or coating layer 3);
2. Depositing an inert material 7 between individual tips;
3. Attaching binding chemistry (—X) onto just the tips; and
4. Attaching Haptan species onto the tips.

1. Gold Coated Polymer Substrate Fabrication and Cleaning

A thin layer of chromium (2 to 3 mm in thickness) was deposited onto the PMMA substrate to act as an adhesion layer. Vanadium can also be used in place of chromium as an adhesion layer. Likewise, amine and thiol chemicals are known to promote adhesion of gold to a surface.

Figure 25:
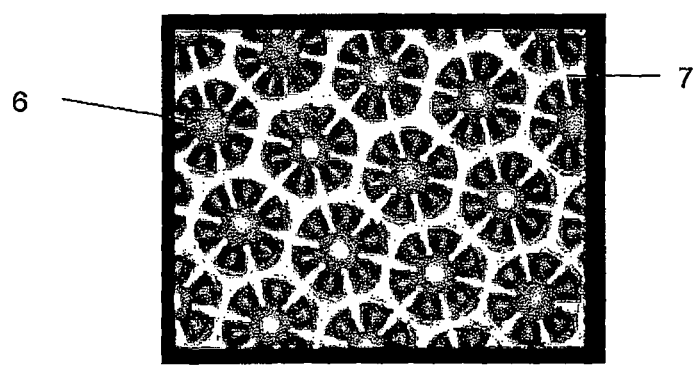
FIG. 25: shows the process for sensor fabrication
Figure 26:
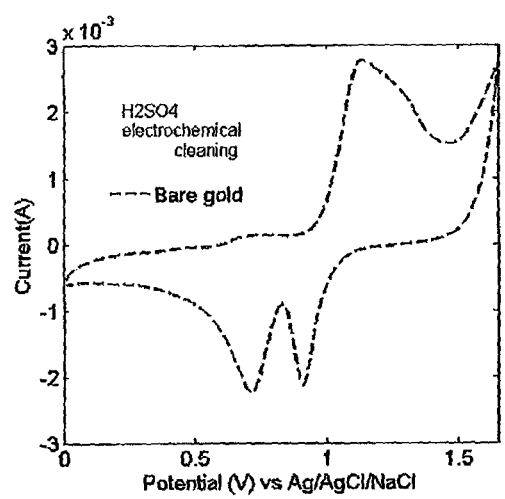
FIG. 26: shows electrochemical cleaning of gold electrodes in sulphuric acid.
Figure 27:
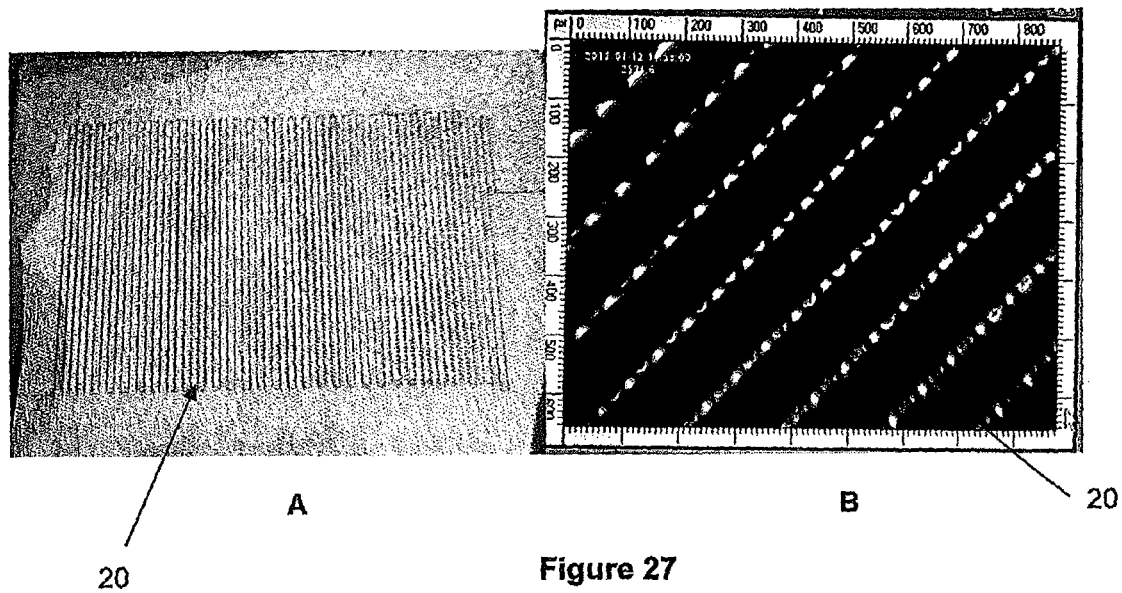
FIG. 27: (A) shows a laser scribed interdigitated array. (B) shows a closer view of the light shining through the 5 micron laser scribed lines.

Gold was then sputtered onto the PMMA substrate to give the electrode with a continuous 3D gold surface depicted in FIG. 25. The electrode was cleaned electrochemically by holding it at 1.65V vs. Ag/AgCl for 15 s in 0.5M $H_2SO_4$, and then cycling between 0V to 1.65 V. FIG. 26 shows a typical CV, and a stable gold oxidation and reduction peak at 1.15 V and 0.9V respectively, thus providing support that gold had been deposited onto the PMMA substrate. The gold coating layer 3 so formed was between about 7 to about 40 nm thick. Gold tracks were then defined into the gold by laser scribing. An example of inter-digitated tracks 20 is shown in FIG. 27 (and is depicted as 20 in FIGS. 4B and C, FIGS. 5A and B and FIG. 6F). The lasered pattern electrically isolates individual areas of the microarray from each other, resulting in the formation of more than one electrode in a single microarray.

2. Depositing an Inert Material 7 Between Individual Tips

Three separate methods were used to deposit the inert material onto the continuous 3D gold surface so as to act as an isolation layer between the tips:
A. Deposition of a photoresist layer (SU-8) over the entire structure, followed by reactive ion etching to expose the gold tips;
B. Deposition of a hydroxylated self-assembled monolayer (SAM-OH) over the entire structure and physical removal of the tip region by rubbing; and
C. Coating the gold coated substrate with a paint layer of suitable viscosity so as to run off the tips before cross-linking. This resulted in the valleys between the tip being filled and the gold surface on the tips left exposed.

All three methods resulted in the gold tips protruding out of the inert material.

A. Deposition of a SU-8 Photoresist Layer

A 100 micron thick layer of SU-8 was applied to a 10 cm wafer of gold coated substrate which had been previously laser scribed into 1 cm inter-digitated sensor chips (FIG. 5C). The SU-8 was then cross-linked under ultra violet light and controllably etched by reactive ion etching. This was found to give very good control of the thickness of the SU-8 polymer layer and also very clean gold tips. FIG. 35B shows two adjacent tips. The tip shown on the right hand side has bare gold, while the tip shown on the left hand side has had a carboxylated polyterthiophene layer electrochemically deposited onto the gold. FIG. 35A shows adjacent tracks of an inter-digitated array in which alternating tracks have carboxylated polytherthiophene deposited onto the tips.

B. Deposition of a Self-Assembled Monolayer (SAM)

Self-assembled monolayer's (SAM) are well known in the art and typically form spontaneously on a substrate by chemisorption of "head groups" onto the substrate followed by slow organisation of "tail groups".

Terthiophene substituted with an alkyl alcohol and $HS(CH_2)_6OH$ are examples of suitable hydroxylated self-assembled monolayer's for use in the present invention.

Figure 28:
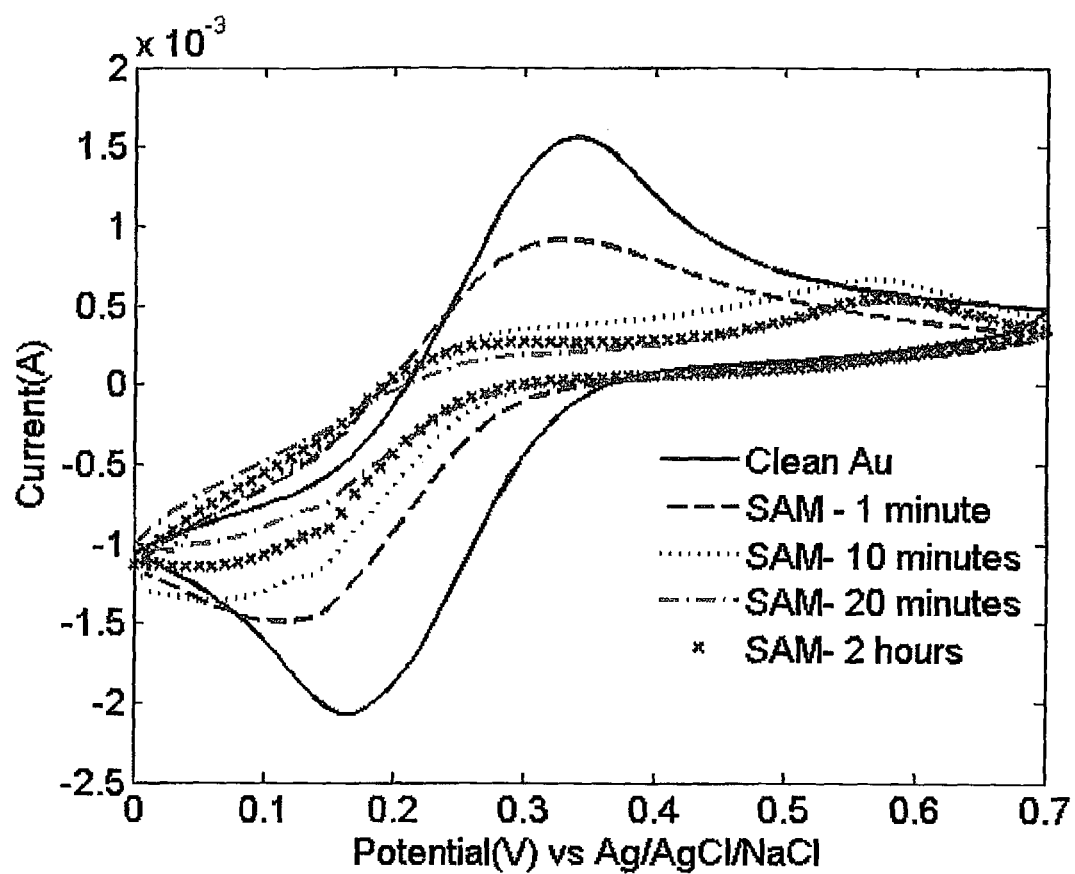
FIG. 28: shows SAM adsorption on an Au electrode over time.

The continuous 3D gold surface of micro-electrodes were subjected to cyclic voltammetry in Potassium ferricyanide ($K_3FeCN_6$) solution. The CV showed a standard ferricyanide oxidation and reduction peak at 0.35 V and 0.15 V respectively. The electrodes were then immersed in solution containing 5 mM SAM-OH in 1:1 ethanol/water solution. The electrodes were then taken out periodically and washed with water and subjected to cyclic voltammograms in 5 mM Potassium ferricyanide solution with KCl supporting electrolyte (FIG. 28). The CV showed gradual disappearance of the ferricyanide peak as the length of time the electrodes were immersed in the SAM solution was increased indicating the gradual adsorption of SAM onto the continuous 3D gold surface of the electrodes.

After a period of 20 minutes the current reached a steady state value showing that the electrodes were saturated with SAM. The CV of the electrode after 20 minutes of SAM adsorption had similar characteristics as the CV of the electrode after 2 hours of SAM adsorption.

Physical removal of the SAM-OH by rubbing the tips on a glass microscope slide resulted in the gold on the tips being exposed. CV in 5 mM Potassium ferricyanide solution showed the typical reduction oxidation peak at significantly reduced current. This indicated that only the gold on the tips was exposed.

The SAMs can be removed from the gold-coated substrate, allowing the substrate to be freshly coated with a new SAM. Thus, the arrays of the present invention can be used a number of times without degradation of the array.

C. Coating the Gold Coated Substrate with an Epoxy Coat

Figure 29:
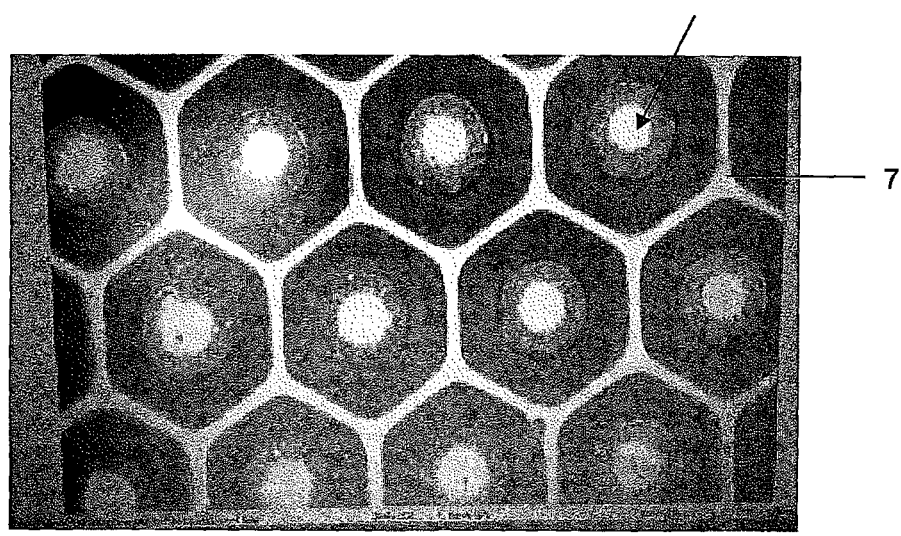
FIG. 29: shows 40 micron tips coated with epoxy.

FIG. 29 shows the gold coated substrate material with a layer of epoxy in the valleys between the tips. The consistency of the epoxy layer provided sufficient time for the epoxy to run off the gold tips prior to cross-linking.

CV in 5 mM Potassium ferricyanide solution showed the typical reduction oxidation, and was evidence that the gold tips were uncoated.

3. Attaching the Binding Chemistry (—X) onto the Tips

Figure 24:
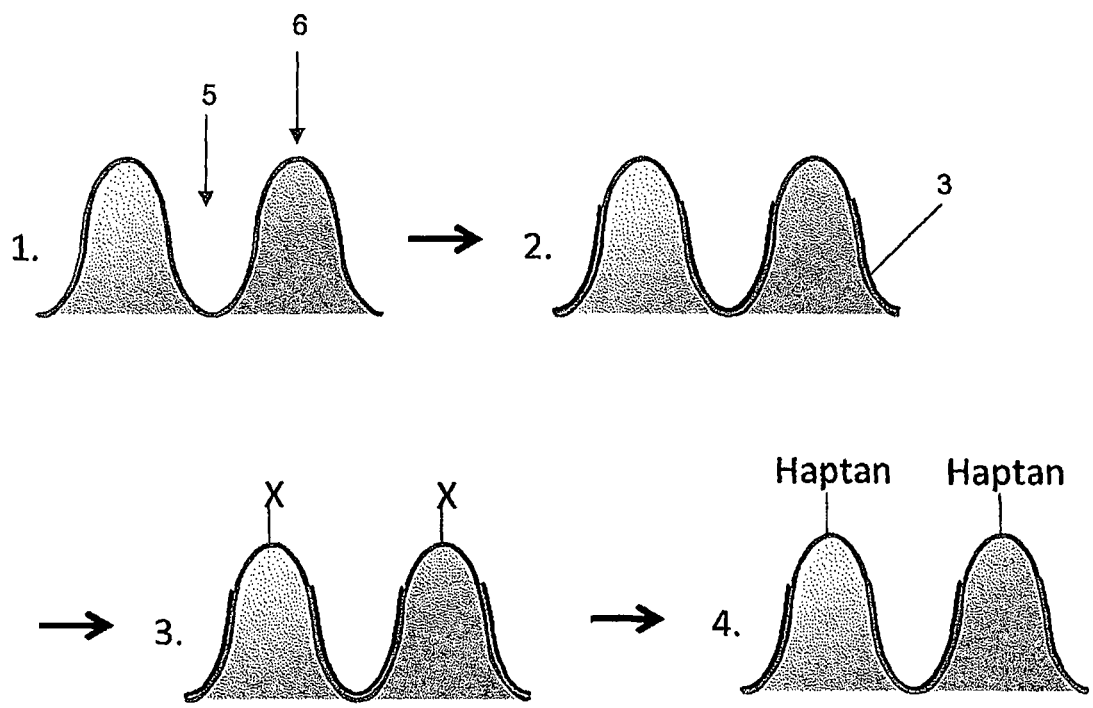
FIG. 24: shows the process for sensor fabrication.
Figure 30:
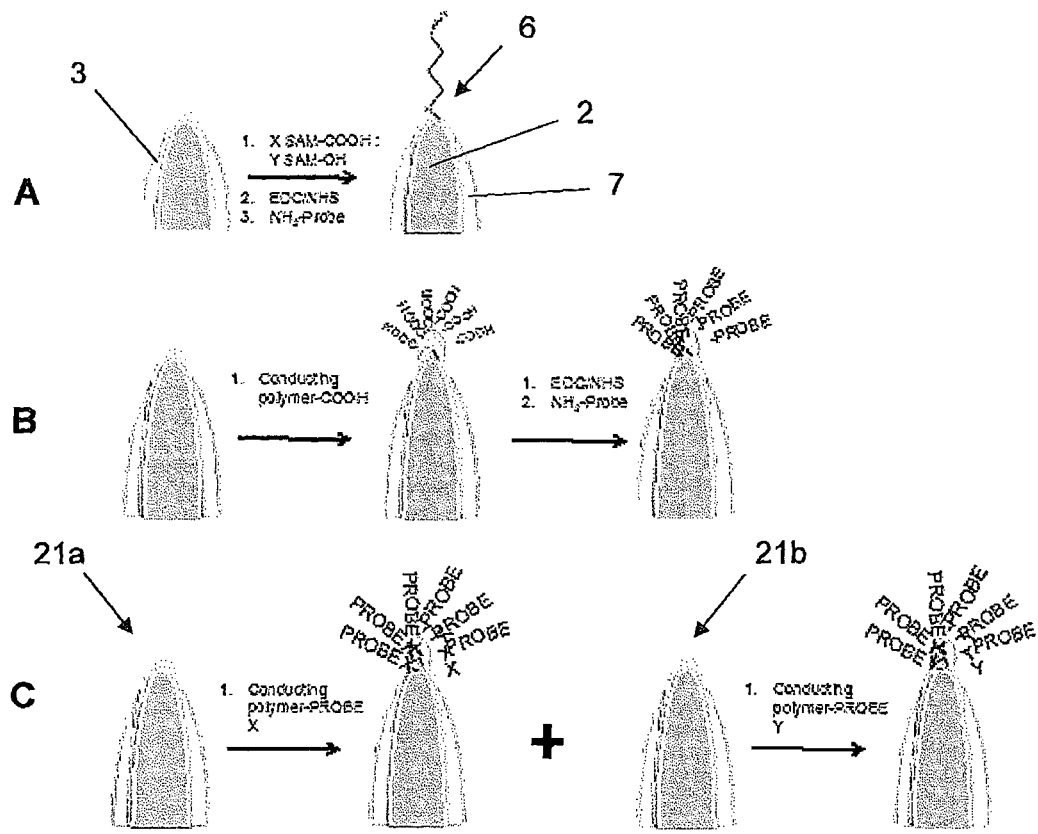
FIG. 30: (A) shows chemical attachment of a SAM via thiol-gold chemistry; (B) shows electrochemical deposition of a conducting polymer followed by coupling to a probe; (C) shows controlled electrochemical deposition of different probes to conducting polymers for multiplexing of capture agents.

The binding chemistry (—X, c.f. FIG. 24) was attached to the tips of the SU-8, SAM-OH or the epoxy coated continuous 3D gold surface of the substrate. Where SU-8 or an epoxy coat was employed as the inert material 7, attachment of the binding chemistry was achieved by electrochemically depositing carboxylated polytherthiophene or animated polyterthiophene onto the tips (FIGS. 30B and C). While FIG. 30C shows the controlled electrochemical deposition of different probes to conducting polymers for multiplexing of capture agents, this can also be achieved using a carboxylic SAM and altering the potential of the different working electrodes as would be apparent to those skilled in the art. Where SAM-OH was employed as the inert material 7, attachment of the binding chemistry was achieved by exposing the tips to SAM-COOH (FIG. 30A). In each case, this resulted in the attachment of either a —COOH or —NH$_2$ group at the end of each of the tips. Use of terthiophene (or pyrrole) substituted with a carboxyl terminated side chain also allows the binding group to be added selectively at a defined tip as it can be electrochemically polymerised on those tips.

To test the selectivity of the process for attaching the binding chemistry onto the tips, 1 micron aminated polystyrene beads were covalently attached via the appropriate linker chemistry.

Figure 31:
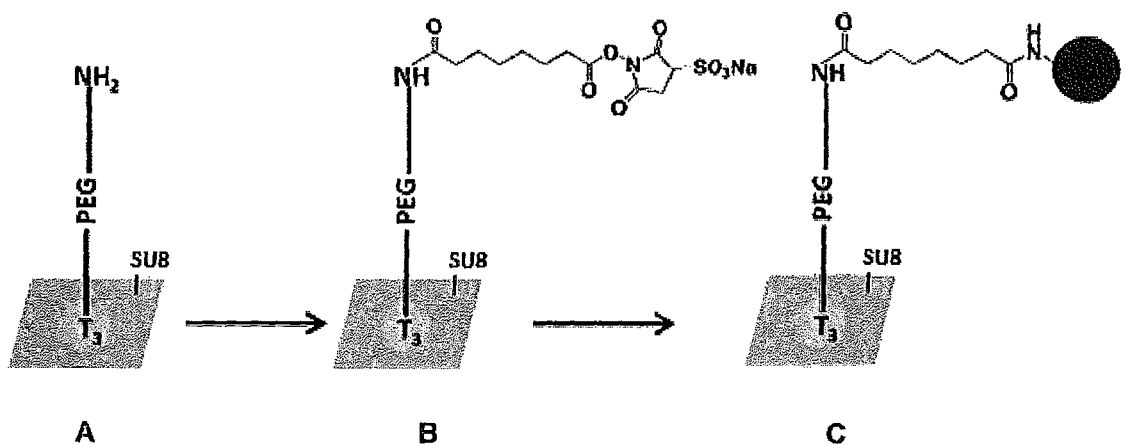
FIG. 31: shows a schematic diagram for attachment of the 1 micron animated blue polystyrene beads to the tips of a sensor array.
Figure 32:
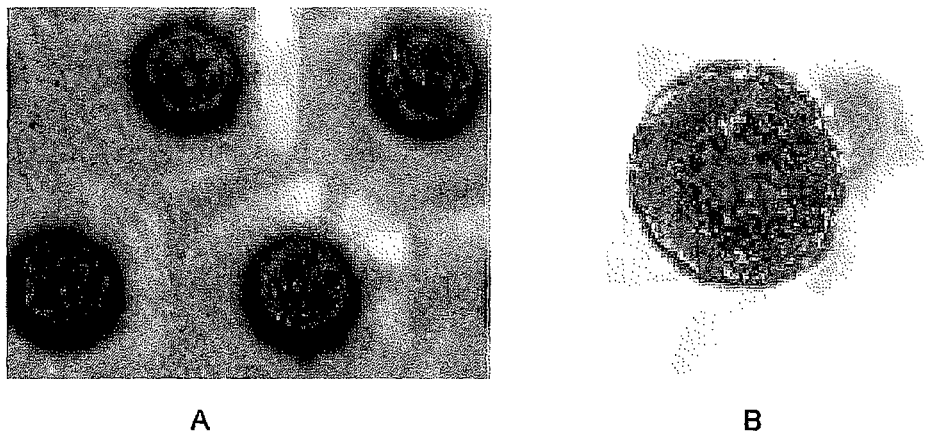
FIG. 32: shows beads covalently attached to the tips of a sensor array.

FIG. 31 illustrates the process for the amine functionalised tips (A). The aminated substrate was exposed to a bi-functional linker solution (6 mg linker/0.5 ml PBS), and shaken at room temperature for 45 minutes. After washing, the substrate was immersed into a solution containing a blue H$_2$N-Bead solution (30 µl beads suspension in 0.5 ml PBS), and shaken at room temperature for 1 h. Attachment of the blue beads onto the array of tips (A) and onto a single tip (B) is shown in FIG. 32. Visual or electrochemical (for example resistance, CV or impedance) techniques can be used to detect what is bound to the arrays.

4. Attaching the Haptan Species onto the Tips

Once confirmation that the attachment chemistry had been bound to the tips of the array, standard linker chemistry could be used to attach a variety of haptans including, but not limited to, antibodies, DNA and cells.

Figure 36:
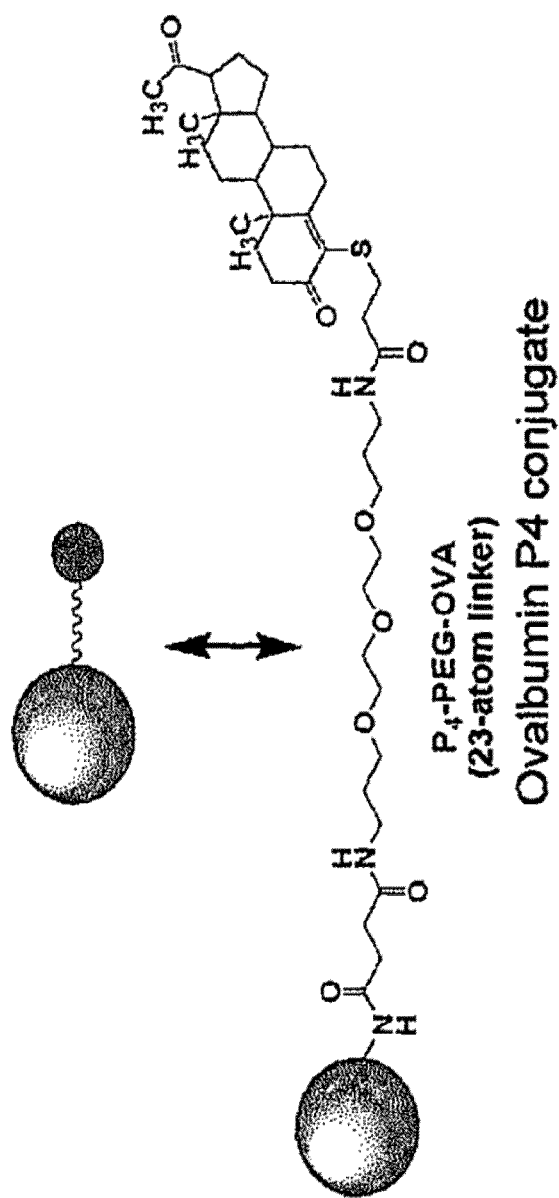
FIG. 36: shows a step in an example method for fabricating a sensor for Progesterone (P4).

As an illustration, the following shows the use of the method to fabricate a sensor for Progesterone (P4). The steps include:

1. Attaching P4 onto ovalbumin to form a conjugate (see FIG. 36);
2. Immersing NH$_2$ substituted arrays into a bi-functional linker solution (6 mg linker/0.5 ml PBS) and shaking at room temperature for 45 minutes to give an activated array (see FIG. 37A);
3. Adding P4-PEG-OVA (0.4 ml solution in 0.2 ml PBS) and allowing it to react for two hours with shaking to give the Haptan functionalised array (II) (see FIG. 37B); and
4. Exposing the array to the P4 primary antibody, and then a secondary antibody with attached beads (FIG. 37C). The attachment of the secondary antibody bead conjugate allows the successful bonding of the primary antibody to be visually confirmed.

Figure 33:
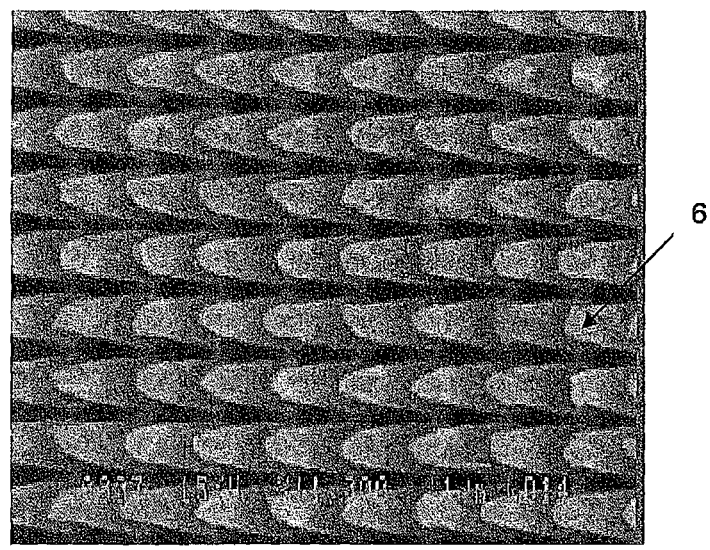
FIG. 33: shows a gold coated nickel 1 micron sensor array.

Development of Arrays According to the Sixth Aspect:

Arrays according to the sixth aspect of the present invention were prepared by sputtering a thin layer (7 nm) of gold onto a polymer substrate, electroplating a thick layer (1 mm) of nickel onto the gold, separating the nickel and polymer layers and sputter coating the nickel with gold. FIG. 33 shows an SEM of a 1 micron gold coated nickel array.

The process provided a substrate which had a gold surface similar to that of the arrays formed according to the fourth and fifth aspects of the present invention and as shown in FIG. 25, and which could be coated in an identical manner with an inert material.

The arrays according to the sixth aspect of the present invention have the advantage of being more robust due to the thickness of the metal base. Also, the metal layer can be laser scribed to isolate groups of tips for selective functionalisation of isolated areas. For the production of sensors using electrochemical detection this ability to scribe is an advantage as it allows the electrodes and the spacing between those electrodes to be defined on a single chip and down to the accuracy of the laser. This approach is widely used in the fabrication of a wide range of electrochemical sensors including those for monitoring glucoses for diabetes, and dramatically simplifies the mass-production.

Using the above described process, arrays including 3 micron tips (25 micron at their base), 0.2 micron tips (1.5 micron at their base and 10 nm tips (160 nm at their base) have also been produced. It has been found that the smaller tip size is favoured with respect to sensitivity of the arrays.

Example Three: Use of a Single Microarray in Multiplexing Assays

Figure 5:
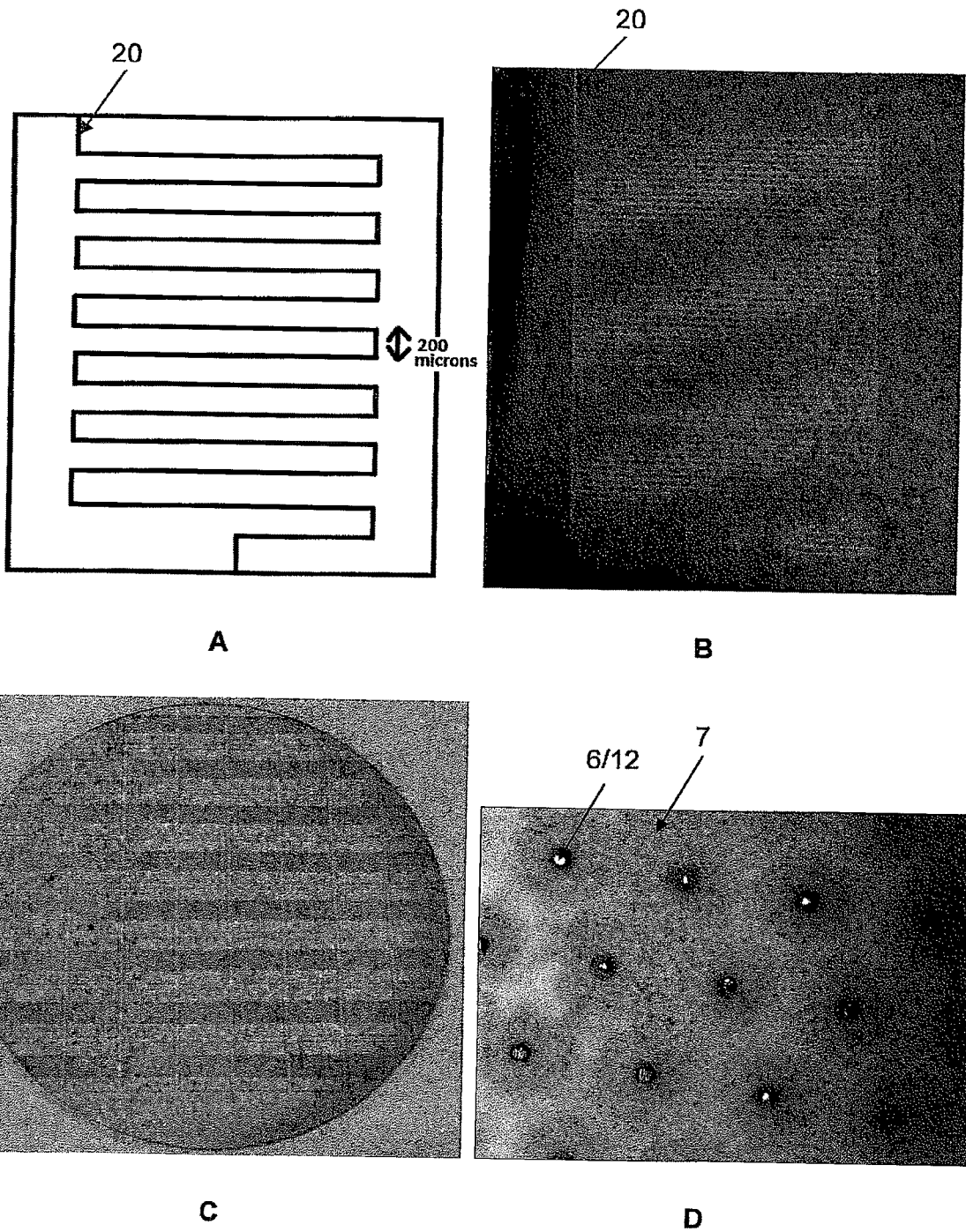
FIG. 5: (A) shows a schematic of the laser pattern for an inter-digitated array; (B) shows an example of the laser patterning on a 2 cm×2 cm gold coated sensor chip; (C) shows a 10 cm disc of sensor chips; and (D) shows a microelectrode array comprising isolated gold tips.
Figure 35:
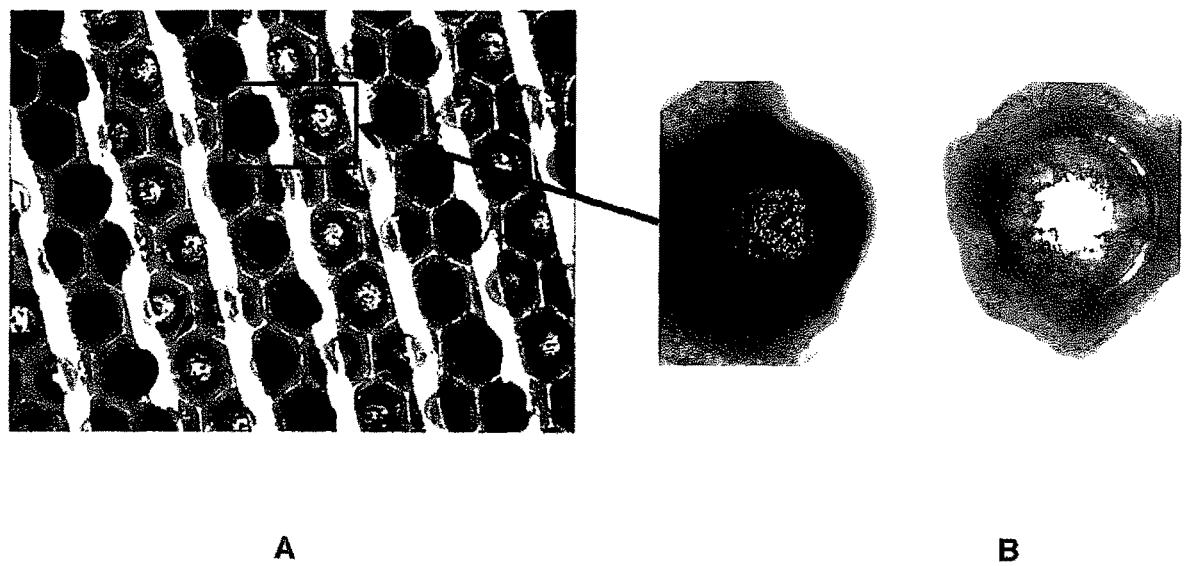

Laser scribing was utilized to isolate individual microelectrodes of an array to form an electrochemical version of the typical DNA or RNA microarray (FIGS. 5, 27 and 35). Groups of micro-electrodes were also isolated to form smaller micro-electrode arrays within a larger array, thus constituting a platform of multiple working electrodes, reference electrodes and counter electrodes. This enabled multiplexing on a single sensor chip or array (as depicted in FIG. 6F).

For example, one sensor chip design was functionalised with different capture agents on each of eight working electrodes to constitute a liver panel on one chip. The antibodies used had affinity for ALT, AST, ALP, GGT, LDH, Hep A, Hep B x-antigen, and full length Hep C E2 protein on working electrodes 1 to 8, respectively. An enzyme, glucose oxidase was tethered to working electrode 9 for detection of serum glucose. The tenth working electrode was a redox electrode to measure non-adhered bilirubin concentration in solution.

In another example, one working electrode array was functionalised with an RNA complement for the srm gene messenger RNA, a second working electrode was functionalised with 3'UTR of srm for targeting microRNA detection, and a third working electrode was functionalised with an antibody raised against the srm gene product spermadine synthase.

The above describes the formation of arrays on a substrate material, including functionalisable areas that are accurately defined in desired patterns and/or shapes at a milli- to nano-meter scale.

The foregoing describes the invention including preferred forms thereof. Modifications and alterations as would be readily apparent to a person skilled in this particular art are intended to be included within the spirit and scope of the invention described.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The invention claimed is:

1. A microarray structure including:
   a substrate material layer;
   a continuous three-dimensional (3D) surface layer on the substrate material layer that:
   is formed from an electrically conductive material and comprises a first electrode; and
   includes accurately defined and functionalisable isolated areas having millimeter to nanometer sized tips on the 3D surface layer, wherein the tips are interconnected within the microarray structure by the 3D surface layer, and wherein the tips protrude through, are exposed above, and are isolated by, an inert material between the accurately defined and functionalisable isolated areas;

a counter electrode electrically isolated from the first electrode within the microarray structure; and a conductive electrolytic solution;

wherein when the microarray structure contacts the conductive solution and current is passed between the counter electrode and the first electrode, the current passes via the conductive solution; and wherein the inert material is on the 3D surface layer and is separated from the substrate layer by the 3D surface layer.

2. The microarray of claim 1, wherein the continuous 3D surface layer is formed from gold, silver, platinum, and/or a carbon based material.

3. The microarray of claim 1, wherein the inert material is also an insulating material.

4. The microarray of claim 1, wherein the microarray is a micro-electrode sensor array which senses a target analyte in the conductive solution.

5. The microarray of claim 1, wherein the 3D surface layer covers the substrate material layer such that the substrate layer is not exposed from above.

6. The microarray of claim 1, wherein the first electrode is a first region of the tips of the 3D surface layer, and wherein the counter electrode is a second region of the tips of the 3D surface layer.

7. The microarray of claim 1, further comprising binding chemistry at one or more functionalisable isolated areas.

8. The microarray of claim 1, wherein the microarray structure is functionalised to be a microelectrode sensor array for analysis of a target analyte in the conductive solution.

9. The microarray of claim 1, further comprising a capture agent at one or more functionalisable isolated areas.

10. The microarray of claim 1, wherein the substrate layer forms a first layer of the microarray structure, and wherein the inert material forms a non-continuous second layer that is separate from the first layer.

11. A microarray structure including:
a substrate material layer;
a continuous three-dimensional (3D) surface layer on the substrate material layer that:
is formed from an electrically conductive material and comprises a first electrode; and
includes accurately defined and functionalisable isolated areas having millimeter to nanometer sized tips on the 3D surface layer,
wherein the tips are interconnected within the microarray structure by the 3D surface layer, and wherein the tips protrude through, are exposed above, and are isolated by, an inert material between the accurately defined and functionalisable isolated areas; and
a counter electrode electrically isolated from the first electrode within the microarray structure, wherein the first electrode is a first region of the tips of the 3D surface layer, and wherein the counter electrode is a second region of the tips of the 3D surface layer;
wherein the inert material is on the 3D surface layer and is separated from the substrate layer by the 3D surface layer.

12. The microarray of claim 11, further comprising a conductive solution, wherein when the microarray structure contacts the conductive solution and current is passed between the counter electrode and the first electrode, the current passes via the conductive solution.

13. The microarray of claim 12, wherein the conductive solution is an electrolytic solution.

14. The microarray of claim 11, further comprising at least one of binding chemistry and a capture agent at one or more functionalisable isolated areas.

15. A microarray structure including:
a substrate material layer;
a continuous three-dimensional (3D) surface layer on the substrate material layer that:
is formed from an electrically conductive material and comprises a first electrode; and
includes accurately defined and functionalisable isolated areas having millimeter to nanometer sized tips on the 3D surface layer,
wherein the tips are interconnected within the microarray structure by the 3D surface layer, and wherein the tips protrude through, are exposed above, and are isolated by, an inert material between the accurately defined and functionalisable isolated areas;
a counter electrode electrically isolated from the first electrode within the microarray structure; and
at least one of binding chemistry and a capture agent at one or more functionalisable isolated areas;
wherein the inert material is on the 3D surface layer and is separated from the substrate layer by the 3D surface layer.

16. The microarray of claim 15, further comprising a conductive electrolytic solution, wherein when the microarray structure contacts the conductive solution and current is passed between the counter electrode and the first electrode, the current passes via the conductive solution.

17. The microarray of claim 15, wherein the first electrode is a first region of the tips of the 3D surface layer, and wherein the counter electrode is a second region of the tips of the 3D surface layer.

18. A microarray structure comprising:
a first layer comprising a substrate material;
a second layer comprising an inert material;
an electrically conductive continuous three-dimensional (3D) surface layer on the first layer, the 3D surface layer isolating the first layer from the second layer, wherein the 3D surface layer protrudes through the second layer as functionalisable, isolated nanometer- to micrometer-sized tips;
a first electrode comprising a first region of the functionalisable, isolated nanometer- to micrometer-sized tips; and
a counter electrode comprising a second region of the functionalisable, isolated nanometer- to micrometer-sized tips;
wherein the first region and the second region are electrically isolated from one another.

19. The microarray of claim 18, wherein the microarray structure is functionalised to be a microelectrode sensor array for analysis of a target analyte in a conductive solution.

20. The microarray of claim 18, further comprising a conductive solution, wherein when the microarray structure contacts the conductive solution and current is passed between the first electrode and the counter electrode, the current passes via the conductive solution.

21. The microarray of claim 18, wherein the conductive solution is an electrolytic solution.

22. The microarray of claim 18, further comprising at least one of binding chemistry and a capture agent at one or more tips.

* * * * *